(12) United States Patent
Khouri et al.

(10) Patent No.: US 11,793,245 B2
(45) Date of Patent: Oct. 24, 2023

(54) BRASSIERE WITH SLIDABLE RIMS

(71) Applicant: Lipocosm, LLC, Key Biscayne, FL (US)

(72) Inventors: Roger K. Khouri, Key Biscayne, FL (US); Khalil R. Khouri, Key Biscayne, FL (US); Thomas Morgan Biggs, Jr., Houston, TX (US)

(73) Assignee: LIPOCOSM, LLC, Key Biscayne, FL (US)

( * ) Notice: Subject to any disclaimer, the term of this patent is extended or adjusted under 35 U.S.C. 154(b) by 0 days.

(21) Appl. No.: 17/534,554

(22) Filed: Nov. 24, 2021

(65) Prior Publication Data
US 2022/0175055 A1 Jun. 9, 2022

Related U.S. Application Data

(60) Provisional application No. 63/122,016, filed on Dec. 7, 2020.

(51) Int. Cl.
*A41C 3/10* (2006.01)
*A61B 90/00* (2016.01)
(Continued)

(52) U.S. Cl.
CPC ............... *A41C 3/10* (2013.01); *A61B 90/02* (2016.02); *A61H 9/0057* (2013.01);
(Continued)

(58) Field of Classification Search
CPC . A41C 3/10; A61B 90/02; A61B 2017/00796; A61H 9/0057;
(Continued)

(56) References Cited

U.S. PATENT DOCUMENTS

| 936,434 A | 10/1909 | Eganhouse |
| 3,382,867 A | 5/1968 | Reaves |

(Continued)

FOREIGN PATENT DOCUMENTS

| CA | 2 827 067 | 8/2012 |
| CH | 396 311 | 7/1965 |

(Continued)

OTHER PUBLICATIONS

PCT/US2019/0654890 International Search Report (dated Dec. 23, 2019).

(Continued)

*Primary Examiner* — Timothy A Stanis
*Assistant Examiner* — Matthew R Moon
(74) *Attorney, Agent, or Firm* — Neil D. Gershon

(57) ABSTRACT

A brassiere including a first aperture, a second aperture, a first shell and a second shell. The first shell has a first rim extending laterally outwardly therefrom, the first aperture dimensioned and configured to receive one or both of the first shell and first rim. The first rim non-fixedly positionable in contact with skin of a wearer. The second shell has a second rim extending laterally outwardly therefrom. The second aperture is dimensioned and configured to receive one or both of the second shell and second rim, the second rim non-fixedly positionable in contact with skin of the wearer wherein the first and second rims are slidable outwardly while maintaining contact with the skin.

19 Claims, 24 Drawing Sheets

(51) Int. Cl.
*A61H 9/00* (2006.01)
*A61B 17/00* (2006.01)

(52) U.S. Cl.
CPC .............. *A61B 2017/00796* (2013.01); *A61H 2201/165* (2013.01); *A61H 2205/082* (2013.01)

(58) Field of Classification Search
CPC ....... A61H 2201/165; A61H 2205/082; A61M 16/0605; A61M 16/0616
See application file for complete search history.

(56) References Cited

U.S. PATENT DOCUMENTS

| | | | |
|---|---|---|---|
| 4,635,618 A * | 1/1987 | Munz | A61H 9/005 601/6 |
| 4,848,364 A | 7/1989 | Bosman | |
| 5,415,620 A | 5/1995 | Chen | |
| 5,536,233 A | 7/1996 | Khouri | |
| 5,662,583 A | 9/1997 | Khouri | |
| 5,676,634 A | 10/1997 | Khouri | |
| 5,695,445 A | 12/1997 | Khouri | |
| 5,701,917 A | 12/1997 | Khouri | |
| 6,042,537 A | 3/2000 | Kaiser | |
| 6,074,399 A * | 6/2000 | Wallace | A61B 17/442 606/122 |
| 6,478,656 B1 | 11/2002 | Khouri | |
| 6,500,112 B1 | 12/2002 | Khouri | |
| 6,558,314 B1 * | 5/2003 | Adelman | A61B 17/02 600/37 |
| 6,641,527 B2 | 11/2003 | Khouri | |
| 6,699,176 B1 | 3/2004 | Khouri | |
| 6,949,067 B1 | 9/2005 | Dann et al. | |
| 7,929,805 B2 | 4/2011 | Wang et al. | |
| 8,485,192 B2 | 7/2013 | Davidson et al. | |
| 9,066,795 B2 | 6/2015 | Khouri | |
| 9,498,565 B2 | 11/2016 | Nowroozi et al. | |
| 9,522,058 B2 | 12/2016 | Khouri | |
| 10,433,947 B2 | 10/2019 | Khouri et al. | |
| 10,603,161 B2 | 3/2020 | Horne et al. | |
| 2001/0031911 A1 | 10/2001 | Khouri | |
| 2003/0073951 A1 | 4/2003 | Morton et al. | |
| 2005/0008669 A1 | 1/2005 | Chen | |
| 2005/0059853 A9 | 3/2005 | Kochamba | |
| 2005/0101222 A1 * | 5/2005 | Cope | A41C 3/10 450/1 |
| 2005/0245850 A1 * | 11/2005 | Freyre | A61F 5/41 128/898 |
| 2005/0267386 A1 | 12/2005 | Copelan | |
| 2006/0106334 A1 | 5/2006 | Jordan et al. | |
| 2007/0055179 A1 | 3/2007 | Deem | |
| 2007/0149991 A1 | 6/2007 | Mulholland | |
| 2009/0042477 A1 | 2/2009 | Redenius | |
| 2009/0177134 A1 | 7/2009 | Timothy | |
| 2011/0251602 A1 | 10/2011 | Anderson | |
| 2011/0313412 A1 | 12/2011 | Kim et al. | |
| 2012/0310126 A1 | 12/2012 | Bureau et al. | |
| 2014/0094722 A1 | 4/2014 | Wu | |
| 2014/0144450 A1 | 5/2014 | Aarestad | |
| 2014/0288646 A1 | 9/2014 | Khouri et al. | |
| 2014/0378946 A1 * | 12/2014 | Thompson | A61M 1/067 604/74 |
| 2015/0328380 A1 | 11/2015 | Furrer et al. | |
| 2016/0000551 A1 | 1/2016 | Khouri et al. | |
| 2016/0324666 A1 | 11/2016 | Barberio | |
| 2017/0196756 A1 * | 7/2017 | Palomäki | A61H 9/0057 |
| 2017/0296422 A1 | 10/2017 | Park et al. | |
| 2017/0341334 A1 | 11/2017 | Corrigan et al. | |
| 2018/0021492 A1 | 1/2018 | Furrer et al. | |
| 2020/0375839 A1 * | 12/2020 | Kim | A61M 1/80 |
| 2020/0405925 A1 | 12/2020 | Koster et al. | |
| 2021/0046227 A1 | 2/2021 | Bakker-Van Der Kamp et al. | |
| 2021/0060220 A1 | 3/2021 | Chang et al. | |
| 2021/0220535 A1 | 7/2021 | Ochiai et al. | |

FOREIGN PATENT DOCUMENTS

| | | |
|---|---|---|
| CN | 103689822 | 4/2014 |
| CN | 108042862 | 5/2018 |
| EP | 2 377 475 | 10/2011 |
| JP | H 1052886 | 2/1998 |
| WO | WO 01/58361 | 8/2001 |
| WO | WO 2005/079612 | 9/2005 |
| WO | WO 2017/165215 | 9/2017 |
| WO | WO 2017/220997 | 12/2017 |
| WO | WO 2020/073021 | 4/2020 |

OTHER PUBLICATIONS

Supplementary European Search Report Application No. EP 19 86 8805 dated Nov. 19, 2021.
Supplementary European Search Report Application No. EP 13 78 5140 dated Feb. 18, 2021.
PCT/US2021/060680 International Search Report (dated Feb. 18, 2022).
English translation of Liu (CN 108042862 A) (Year:2018).
www.amazon.com/Motherlove-Certified-Organic-Cracked-Nursing/dp/B0007CQ726.

* cited by examiner

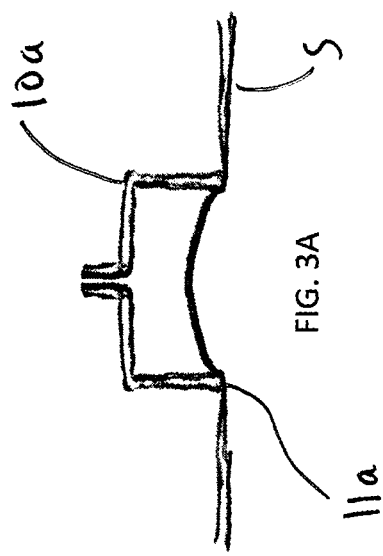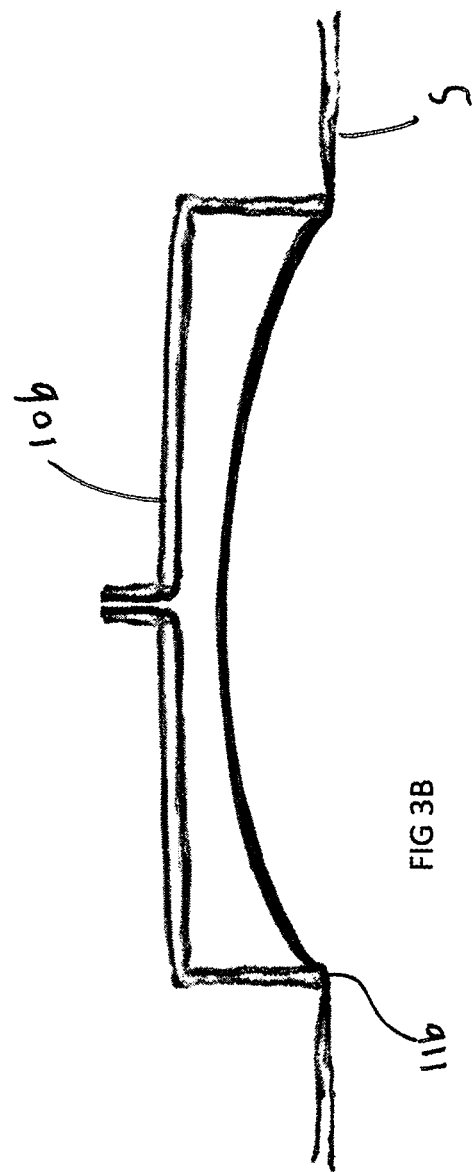

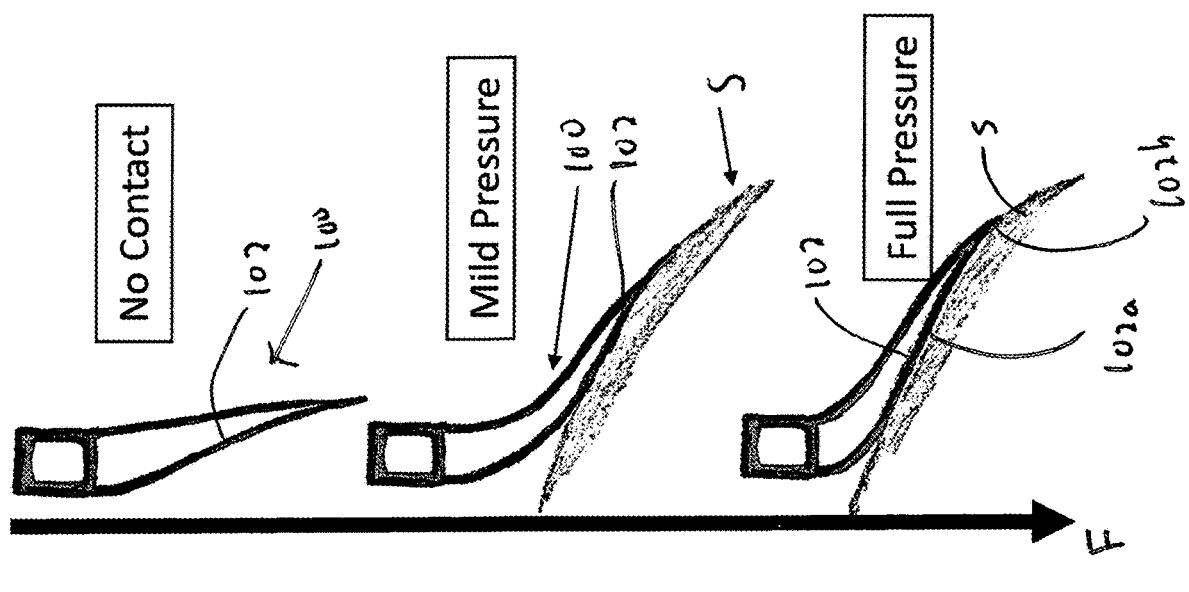

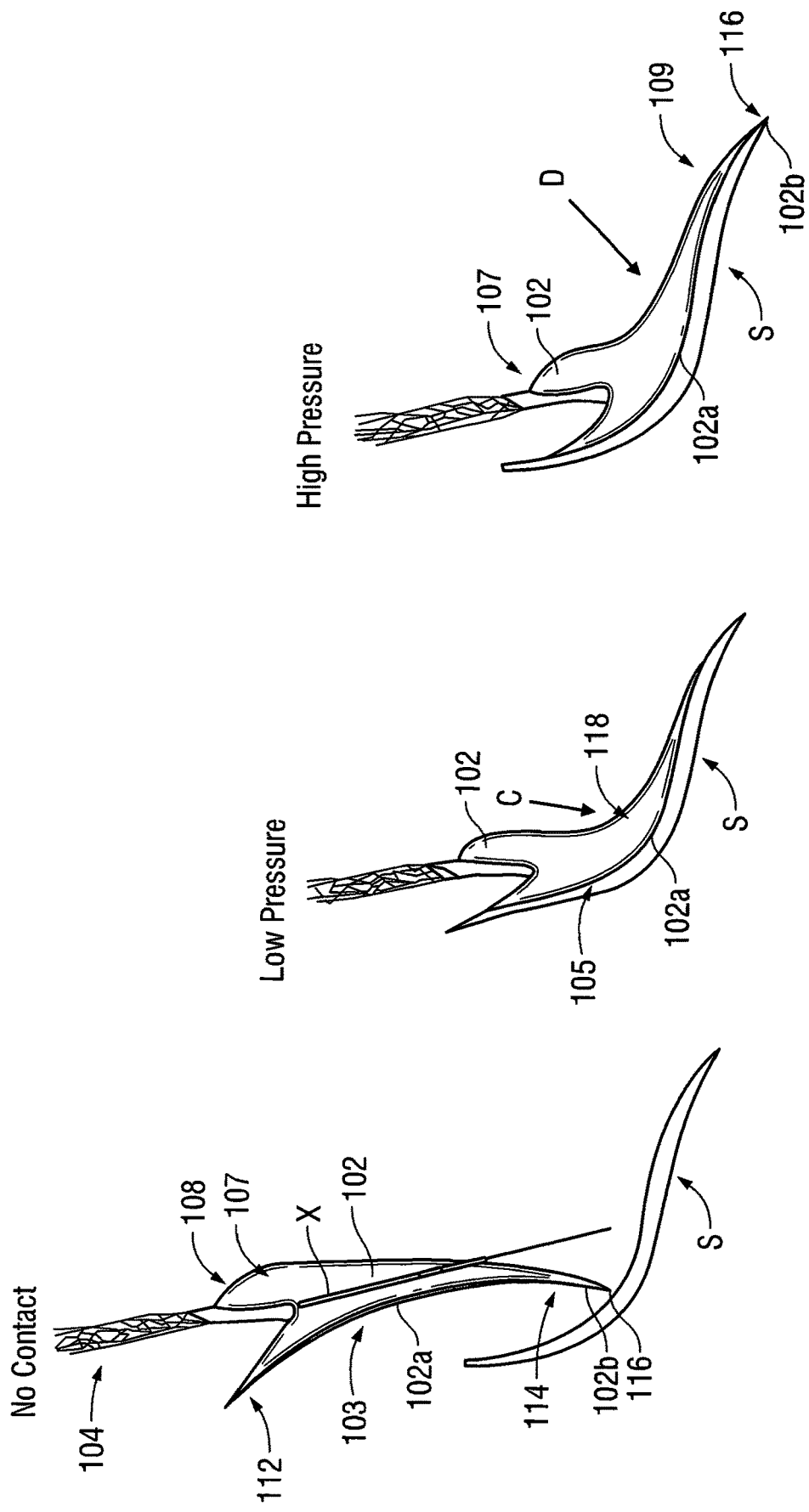

BRASSIERE WITH SLIDABLE RIMS

This application claims priority to provisional application Ser. No. 63/122,016, filed Dec. 7, 2020, the entire contents of which are incorporated herein by reference.

BACKGROUND

Field of the Invention

This application relates to brassieres, and, more particularly, to brassieres with apertures to receive shells with outwardly slidable rims.

Background of Related Art

It is a well-established biologic phenomenon that sustained gentle tension is a natural stimulus for tissue growth. We grow during childhood thanks to the tension generated by the epiphyseal growth plate that lengthens our bones. Internal inflatable tissue expanders and Ilizarov bone distractors are examples of widely used medical devices that enlarge tissues based upon this principle. These medical devices, however, require complication-prone invasive surgical procedures. There is therefore a societal need for distraction devices that are external and non-invasive while still capable of enlarging tissue in a safe, practical, and user-friendly manner.

Cosmetic breast augmentation and post mastectomy breast reconstruction are the two conditions where such a non-invasive method of tissue enlargement might find its most common application. Dating back to the 1800's, a very large number of vacuum based breast enlargement devices have tried to achieve this goal. While some have been marketed over the years, they are essentially all considered novelty items and none have ever proven their efficacy in scientific clinical studies because none could be consistently applied for the prolonged period of time required to induce substantial tissue growth.

The Brava device conceived and designed by the inventor of the present invention, disclosed in U.S. Patents such as U.S. Pat. Nos. 6,641,527, 6,500,112, 6,478,656, 5,676,634, 5,695,445, 5,662,583, is the only device known to the inventor with scientifically proven efficacy reviewed by the FDA. The Brava device was successful in inducing permanent tissue growth because the inventor identified the biomechanical constraints involved in maintaining a vacuum over the breast for a prolonged period of time and applied biomedical engineering principles to solve these constraints. While a substantial improvement over the prior art, the Brava device has not replaced breast implants because patient compliance remains a major hurdle. The Brava device is impractical and difficult to use all day, every day for the number of months required to achieve substantial tissue growth. In addition to being bulky and cumbersome, the Brava device also has a few other limitations which have yet to be successfully addressed in its over 25 years of use. Thus, the present inventor has recognized the need for improvement of the Brava device.

There are a number of challenges associated with maintaining vacuum to induce a distractive force over the breast in a sustained fashion over a prolonged period of time to achieve breast enlargement. These three challenges are:

1) Preserving the vacuum by avoiding air leaks despite the complex surface contour of the torso, its wide individual variation, and the significant surface topography changes caused by movement of the torso and shoulders.
2) Balancing the distractive force applied to the breast with the counter-force exerted by the rim of the external vacuum expander (shell/dome) in contact with the surrounding skin to prevent excessive pressure that would collapse capillary circulation and lead to pressure ulcerations.
3) Reducing the shear stresses that develop at the junction between the tensed skin inside the vacuum shell (dome) and the skin firmly held down and anchored by the inner lip of the rim of the shell. These shear forces concentrated at the inner lip of the rim are a major cause of skin irritation, blistering and ulceration.

The inventor's prior Brava device attempted to solve challenge #1 with a soft silicone gel bladder that conformed to the complex contour of the chest wall and absorbed, to a certain extent, the varying surface topography associated with normal activity. To avoid air leaks, the sole of that bladder included an adhesive layer that sealed it with the skin. However, that adhesive layer tended to wear out with daily use. Once the adhesive layer deteriorated, air leaks occurred, thus, the Brava device only provided a short term solution to the air leak challenge.

Realizing that an external pressure above 20 mmHg occludes capillary circulation (20 mmHg is the highest pressure that can be safely tolerated under the rim on a prolonged basis, as described in U.S. Pat. No. 6,500,112), the Brava device attempted to solve balancing the counter-force (challenge #2) by having the surface contact area of the rim being equal to the surface area of the dome aperture where the vacuum pressure is exerted.

The Brava device attempted to solve the shear stress problem challenge (challenge #3) by providing a contact rim that dissipates the shear by recruiting inward some peripheral skin. The larger the aperture, and therefore the amount of tissue under tension, the larger the shear stress.

Shear Stress=$\tau$=Force/Shear Area

Assuming that the Force=$P_{ressure}\times$Surface Area

Approximating the aperture to a circle, the Surface Area $S=\pi R^2$

Force=$P_{ressure}\times\pi R^2$

Shear Area=Circumference ($2\pi$)$\times$Thickness of tissue ($T_{hickness}$)

Shear Stress=$\tau$=Force/Shear Area=$P\times\pi R^2/(2\pi R\times T)$
=$P_{ressure}\times R/T_{hickness}$ If $P_{ressure}$ & $T_{hickness}$ are constant, there is a linear relationship between Radius and Shear Stress The larger the Radius, the higher the Shear Stress.

This is why smaller suction cups, nipple expanders and lactation devices (3-6 cm max.) have little need to address this problem. The skin at the periphery of the breast (at least 10-12 cm aperture diameter) that is anchored down by a rigid rim is under a significant amount of lateral inward stress. Prior to the Brava device, none of the prior art addressed this issue and this might be the reason why none of these devices was ever adopted by the medical community. Since the gel rim of the Brava device has an adhesive sole, to recruit the amount of skin necessary to dissipate the shear stress, the gel rim that is adherent to the skin has to significantly deflect. This proved to be the most difficult issue to solve. For the deflection arc to deliver the required amount of inward recruitment, the gel rim had to be at least 4-5 cm high. It also had to be very compliant, offering little resistance to inward roll. This added bulk, height, weight, and premature wear of the constantly deflecting silicone gel bladder.

None of the over 50 prior art breast enlargement patented devices have features that address the foregoing issues/challenges. In fact, none except the Brava device addresses the counterforce and the shear force, however, even the Brava device has some challenges.

Although suction cups sometimes have rubber rims, the rubber used does not meet the specific durometer and elasticity requirement, and they lack the necessary configuration to meet the counterforce/shear force challenges. Furthermore, they lack sufficient concavity and width. Suction cups are also very different from breast enlargement devices. Their shear stress is minimal compared to breast enlargement devices that are an order of magnitude larger in size. Furthermore, most suction cups are passive as they typically do not have an external vacuum pump—their source of vacuum is the recoil force of the rubber rim itself. Additionally, suction cups are often made of natural rubber which has a high incidence of allergy so are of limited use in medical devices.

U.S. Pat. No. 10,603,161 discloses apparatus and methods for nipple and breast formation. The apparatus uses adhesion to hold the mold in place. The design of the rim does not taper down and lacks sufficient concavity. The devices of the '161 patent have no way of dissipating the larger shear forces that would cause skin blistering. The breast has a larger surface area than the nipple, so the deformation is larger and the force on the perimeter is higher for the same amount of pressure. The amount that the skin needs to stretch (strain) for the nipple is minimal compared to the breast therefore the shear force is also less for the nipple.

U.S. Pat. No. 10,433,947 (same inventor as the inventor of the present invention), discloses methods and devices for tissue expansion. The patent describes a splint that holds a swollen/pre-expanded breast in place as an alternative to expanding with an external vacuum. It states, "Another way of mechanically coupling the splint to the skin is surface tension. Surface tension is the naturally occurring means by which the body holds together tissues that need to remain mechanically coupled but yet glide and avoid shear forces. This is how the expanding rib cage transmits the mechanical force of inhalation to the soft sponge like lungs to expand and this is how bowel loops can glide past another while held together too." However, surface tension is being used here to apply the tensile expansion force on the tissues as an alternative to the glue to replace the need for vacuum or traditional sticky adhesives.

U.S. Pat. No. 5,676,634 (same inventor as the inventor of the present invention) discloses a method and apparatus for soft tissue enlargement with balanced force. The patent discuses a rim with a surface area sized to prevent excessive contact pressure to the skin. The patent does not address shear.

U.S. Pat. No. 6,500,112 (same inventor as the inventor of the present invention) discloses a vacuum dome with a supporting rim and rim cushion. This patent describes minimizing shear force by providing an interface between the dome and the skin which allows inward displacement of the contact surface. This reduces the strain dL/L on the skin. dL is the same but L is larger. The contact surface is no longer anchored by a rigid dome, the flexible interface allows the skin to move more freely with lower strain, lower stress, and lower shear force. However, this device still does not fully meet the challenges enumerated above.

U.S. Pat. No. 9,498,565 discloses lactation devices. Embodiments of the device disclosed include a bra-insert to hold the device in place. Some embodiments include shoulder and torso harnesses, or other strapping fabrics and mechanisms to hold the device in place to allow for hands-free expression. In addition, adhesive fabrics, such as Geckskin™ (University of Massachusetts-Amherst, Amherst, Mass.), to leverage Van der Waals forces on the anterior surfaces of the soft structure 1 of FIGS. 3A & 4A to hold the device in place are disclosed. The patent describes in some embodiments lubricating systems to prevent chafing after repeated uses. Also disclosed are thicker lip shaped structures along the flange of the ellipsoid opening which can include small pores to allow for lubricating fluid to slowly leak upon the user's breast. This lubricating fluid, as described, can also serve as a source of wet adhesion to ensure a proper seal between the device and the user's breast. Some embodiments include user-applied lubrication prior to use or no lubrication can be used. Using lubrication as a means of preventing chafing after repeated uses are disclosed. This is different than using lubricant to reduce shear force. Breast pumps to express milk use a saccadic vacuum that mimics the nursing baby. The chafing from breast nipple pumps is from friction as the nipple is sucked in and out, it is not from shear force. Nipple cream for breast pumps is common. These nipple suckers have limited apertures around the areola and inflict minimal shear stress. https://www.amazon.com/Motherlove-Certified-Organic-Cracked-Nursing/dp/B0007CQ726/&tag=diapersnet-20)

As can be appreciated, the foregoing prior art devices fail to address the drawbacks/challenges enumerated above, and some do not even recognize the importance of, or are not concerned with, shear forces. Therefore, the needs exists for a vacuum expander for tissue expansion that can effectively prevent air leaks to preserve the vacuum, prevent excessive pressure that would collapse capillary circulation and reduce the shear stresses that develop at the junction of the skin. The devices should also be comfortable to wear for extended periods and minimize skin irritation and blistering as well as be concealable and wearable as comfortably as a regular padded bra. Such devices could improve breast expansion/augmentation and well as expansion/augmentation of other body tissue. Furthermore, such devices could also be used for breast reconstruction.

SUMMARY OF THE INVENTION

The present invention solves the problems and deficiencies of the prior art. The present invention provides a comfortably wearable dome (or other shaped) device with a specialized rim which contacts the body tissue and utilizes vacuum for tissue expansion, e.g., expansion of breast tissue. The expander devices of the present invention, also referred to herein as vacuum expanders or tissue expanders, effectively 1) preserve the vacuum by preventing air leaks; 2) balance the distractive force applied to the breast with the counter-force exerted by the rim of the external vacuum expander in contact with the surrounding skin to prevent excessive pressure that would collapse capillary circulation and lead to pressure ulcerations; and 3) reduce the shear stresses that develops at the junction between the tensed skin inside the vacuum shell with the skin firmly held down and anchored by the inner lip of the rim to reduce skin irritation, blistering and ulceration which is caused by excess shear forces concentrated at the inner lip of the rim.

It should be appreciated that the devices of the present invention could successfully, with minimal trauma, effect breast expansion/augmentation and well as expansion of other body tissue.

To maintain an air-tight seal, i.e., preserve the vacuum, the devices of the present invention replace the adhesive gel bladder of the Brava device with a deeply concave, wide, tapered, soft rubber skirt that deflects to open and spread out under the effect of the downward vacuum force. This increases the surface contact area and improves the seal. Furthermore, the concave configuration of the skirt rim forces its feathered-out periphery to grip down and espouse the surface contour of the torso to maintain the air-tight seal. This deflective conforming soft rubber skirt can also accommodate a significant amount of body motion without losing the vacuum seal.

The devices of the present invention also effectively balance the distractive and counterforces. Increasing the vacuum pressure causes the concave flexible rubber rim of the device rim to deflect out and widen to increase the surface contact thereby reducing the counter-pressure on the skin. This property of the concave tapered deflecting rubber rim (sole) that increases surface contact with increases in the downward force balances the forces to keep the skin pressure below damaging levels.

The devices of the present invention completely solve the shear stress problem. Because the soft rubber rim maintains a vacuum seal by faithfully espousing the body contour, there is no need for an adhesive layer. Quite the contrary, the device works best when there is a lubricant to provide near friction free gliding between the skin and the rubber rim (skirt) that opens to wrap around the body. With the contact surface no longer glued and anchored to the rim, the skin is free to move, and the tension can recruit as much peripheral skin as necessary to dissipate the damaging shear stress. With this near free tissue recruitment there is lower strain, lower force and lower shear stress. Thus, the vacuum expanders of the present invention solve the shear stress problem by operating in a manner opposite to that of the prior art. The prior art devices focused on securement of the rim position by use of adhesive; the present invention actually "unlocks" the rim and encourages movement/sliding (gliding) of the rim. Thus, the non-adhesive (e.g., lubricated) interface of the rim of the present invention allows it to spread out under the effect of vacuum to increase its contact surface and reduce pressure and to freely recruit peripheral tissue to nullify shear forces.

In accordance with one aspect of the present invention, a tissue expander is provided comprising a shell, an opening in the shell in communication with an external vacuum source to apply a vacuum within the shell and impart a distracting force to expand tissue, and a rim connected to the shell and adapted to be in contact with a skin of a patient. The rim is non-fixedly attached to the skin of the patient and moves laterally outwardly with respect to the shell under application of the vacuum.

In some embodiments, the shell is in the shape of a dome.

In some embodiments, the rim is composed of rubber and has a lubricating layer on a bottom surface to glide over the skin, thereby reducing shear stress between the rim and contact surface of the skin. In other embodiments, the rim has a lubricant to provide reduced friction contact with the skin to allow sliding of the rim. In preferred embodiments, the rim is composed of a synthetic rubber and is of low durometer.

In preferred embodiments, the rim has a non-adherent, non-adhesive lower tissue contact surface.

In some embodiments, the rim has a concave tapered portion that forms a skirt that deflects to open and spreads out laterally (widens). In preferred embodiments, when downward pressure is applied by the vacuum, the rim conforms to the contour of a body of the patient and the rim deflects to increase a surface in contact with the skin and prevent an increase in counter pressure against the skin.

In some embodiments, the rim has a feathered down periphery to wrap around a portion of the body and grip the torso. Other features/aspects that can be incorporated into some embodiments of the rims of the present invention can include one or more of the following: a) a malleable edge thicker than a proximal portion of the rim, the edge being more deflectable than the proximal portion; b) a taper and inward camber so its axis is less than 20 degrees from the vertical; c) of asymmetric form having a narrower skirt medially and a more curved inward skirt laterally to provide a lateral side with deeper concavity and a length longer than a medial side to wrap around the body contour; and/or d) a fin pocket within which thin ribs or fins of proper curvature and durometer can be inserted to help espouse the contour of the lateral torso.

In some embodiments, the rim has a connection mechanism for releasable attachment to the dome (or shell) so that the dome of a first size can be removed from the rim and a dome of a second size can be attached to the rim. In these embodiments, domes (shells) of varying sizes can be selectively connected to the rim. In other embodiments, two or more domes are permanently attached to the rim, the two or more domes being of progressively deeper sizes.

In accordance with another aspect of the present invention, a tissue expander is provided comprising a shell, an opening in the shell in communication with an external vacuum source to apply a vacuum within the shell and impart a distracting force to expand tissue and a rim connected to the shell and adapted to be in contact with a skin of a patient. The rim has a concave lower surface, the concave lower surface deforming upon the application of vacuum to deflect out from its concave condition to invert to a convex shape (condition) upon application of vacuum. That is, the segment under the rim changes from concave to convex while in some embodiments the periphery, especially the lateral side remains concave to preserve the seal.

In some embodiments, the rim has tapered surface to progressively decrease in thickness toward an outer periphery to provide a thinner more malleable edge deflectable to a larger degree than thicker portions of the rim (closer to the dome). Other features that can be incorporated into embodiments of the rims of the present invention can include one or more of a) a taper down to a feather thickness forming a feathered edge b) a lateral side of the rim is longer and has a deeper concavity than a medial side of the rim; c) an inward camber angling downward from a horizontal plane to enhance gripping of the body of the patient; and/or d) an interdigitating design that allows the medial edges of both rims to overlap without leaving any air passage folds that can cause loss of vacuum. In some embodiments, the rim is composed of a low durometer rubber material. In some embodiments, the rim is composed of a varying durometer synthetic rubber material, with the periphery having a lower durometer.

In some embodiments, as downward pressure is applied, the counterforce between the rim and skin is evenly distributed over a skin contact area. In some embodiments, as vacuum pressure increases, the rim increases in deflection to widen and increase contact area with the skin and reduce counter pressure on the skin.

In accordance with another aspect of the present invention, a brassiere is provided comprising a) a first aperture; b) a second aperture; c) a first shell having a first rim extending laterally outwardly therefrom, the first aperture dimensioned and configured to receive the first shell and/or first rim, the first rim non-fixedly positionable in contact with skin of a patient; and d) a second shell having a second rim extending laterally outwardly therefrom, the second aperture dimensioned and configured to receive the second shell and/or second rim, the second rim non-fixedly positionable in contact with skin of the patient. In some embodiments, a distractive force is applied to the skin of the patient within the first and second shells and during such distractive forces the first and second rims slide laterally outwardly while maintaining contact with the skin.

In some embodiments, the rims have a concave lower surface deforming upon application of vacuum to invert to a convex surface.

In some embodiments, the distractive forces are applied by an external vacuum in communication with the shell; in other embodiments, the distractive forces are applied by elastic recoil of the shells and/or rims.

The brassiere can include a reinforcing band to connect the brassiere to the rim and/or reinforcement straps to maintain feathered peripheral edges of the rim in firm contact with the skin to ensure a vacuum seal.

In accordance with another aspect of the present invention, a method for reducing shear stress in a device for expanding tissue is provided. The method comprises positioning a device having a shell and a rim extending from the shell configured for contact with a body of the patient, the rim non-adherently positioned on the body so that upon application of a distracting force within the shell, the rim spreads laterally outwardly with respect to the shell such that shear stress is reduced at a junction between tensed skin inside the shell and skin firmly held own and anchored by the rim.

In some embodiments, the distractive force is applied by elastic recoil of the rim.

In some embodiments, the distractive force is applied by application of a vacuum within the shell. A portable vacuum pump can be provided in communication with an interior of the shell to apply the vacuum. A pressure control mechanism can be provided to control vacuum pressure within the shell. In some embodiments, the pressure control mechanism comprises a manual pump with a pressure relief valve to prevent vacuum pressure from reaching a damaging level. In some embodiments, as vacuum pressure increases, the rim increases in deflection to widen and increase contact area with the skin and reduce counter pressure on the skin.

BRIEF DESCRIPTION OF THE DRAWINGS

So that those having ordinary skill in the art to which the subject invention appertains will more readily understand how to make and use the surgical apparatus disclosed herein, preferred embodiments thereof will be described in detail hereinbelow with reference to the drawings, wherein:

FIGS. 3A and 3B provide illustrative examples of the shear effect of an embodiment of small and large vacuum expander domes (shells) of the prior art;

FIGS. 5A, 5B and 5C are schematic side views of the vacuum expander of an embodiment of the present invention showing its adaptation from no contact (FIG. 5A) to mild pressure (FIG. 5B) to full pressure (FIG. 5C);

FIGS. 7A-7C are schematic side views illustrating the adaptation of the rim of the vacuum expander of an embodiment of the present invention from no contact (FIG. 7A) where the rim has a concave cambered inward curvature, to low pressure (FIG. 7B) as it gradually opens up, to high pressure where it is fully opens (FIG. 7C), the dome shown attached to the rim;

FIGS. 9A and 9B show how the rim of the vacuum expander of an embodiment of the present invention is shaped to wrap around the chest and hug the skin surface contour due to its tapered fins while

DETAILED DESCRIPTION OF PREFERRED EMBODIMENTS

Figures 1A, 1B:
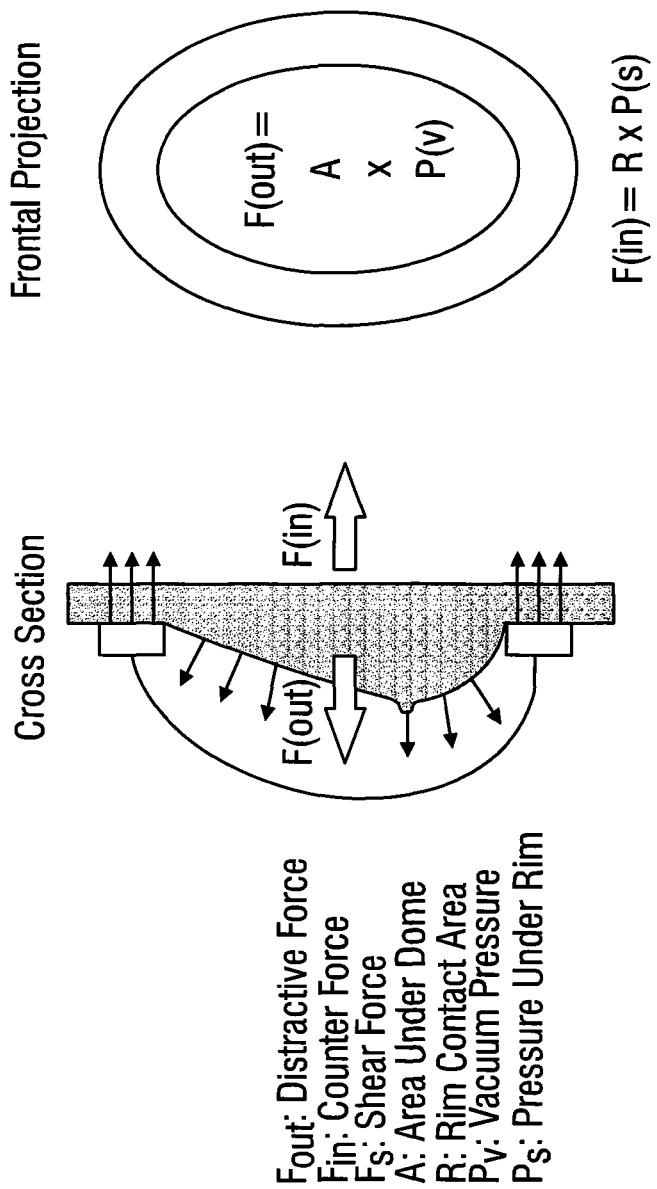
FIGS. 1A and 1B are schematic views of the forces encountered (biophysics) with an external vacuum expander with FIG. 1A showing a cross-sectional view and FIG. 1B showing a front view.

The current invention utilizes advances in materials technology such as in silicone rubber and in urethane and in other synthetic rubber materials technology to provide a solution to all three problems/challenges enumerated in the Background section above:

1) Preserving the vacuum within the dome (shell) by avoiding air leaks despite the complex surface contour of the torso, its wide individual variation, and the significant surface topography changes caused by movement of the torso and shoulders.
2) Balancing the distractive force applied to the breast with the counter-force exerted by the rim of the external vacuum expander in contact with the surrounding skin to prevent excessive pressure that would collapse capillary circulation and lead to pressure ulcerations. (The arrows show in FIG. 1A the distractive force by the vacuum vs the counter force and its relation to the area under the dome and pressure).
3) Reducing the shear stresses that develop at the junction between the tensed skin inside the vacuum shell and the skin firmly held down and anchored by the inner lip of the rim. This reduces skin irritation, blistering and ulceration caused by shear forces concentrated at the inner lip of the rim.

The solutions to each of these problems/challenges (referred to below as #1, #2 and #3) are discussed in detail below. This is achieved by a vacuum expander with a dome (shell) or other shaped device attached to a uniquely designed and configured rim (also referred to herein as a skirt) which interacts with the skin in a unique fashion and functions in ways different from prior and current vacuum expanders. Note solutions to address any one of the aforementioned three problems/challenges provide an improvement over prior and current devices so that the present invention in some embodiments can address only one or only two as well as all three of the problems/challenges.

The tissue expanders of the present invention use pressure from an external vacuum source or from recoil of its rubber rim or semi-rigid shell to impart a distracting force that can expand tissue. The device is composed of a shell (also referred to herein as a dome when dome shaped) which forms a more rigid section for the tissue to expand into and a softer rim which is in contact with the tissue to serve as an interface between the dome and tissue. The rim can have a connection mechanism, for permanent or releasable attachment to the dome. A pump, sensor and servomechanism control vacuum pressure within the dome and the pump communicates with the interior of the dome via a tube(s) from the pump extending to or into an opening in the dome. Alternatively, if the recoil of the rubber rim is used to generate the vacuum, an adjustable pressure release/relief valve can be included to prevent the accumulation of higher vacuum pressures that can be damaging to the tissues.

The prior art teaches the use of adhesive to secure the vacuum expander to the skin. However, the present inventors, after years of study, discovered that the use of adhesive caused various problems, such as those enumerated above. The inventors discovered that providing an opposite effect, that is, to allow the skin under the vacuum expander to glide or slide, rather than be adhesively secured to lock movement, actually provided significant reduction in shear stresses and significantly reduced skin damage from excessive shear forces. Thus, the expanders of the present invention developed by the inventors, which are non-fixedly/non-adhesively attached to the skin, operate in a way not contemplated, and in fact opposite to, the teachings of the prior art. The present inventors also recognized the limitations of current rim configurations and discovered unique features for the rim to improve its adaptation to the wearer's body.

The present invention provides superior results in tissue expansion via vacuum. Such tissue expansion is described below for breast expansion/augmentation, but could also be used for expansion/augmentation of other body tissue.

To maintain an air-tight seal (challenge #1) and balance the distractive force with the counterforce (challenge #2), the devices of some embodiments of the present invention replace the adhesive gel bladder of the prior art with a deeply concave, wide, tapered, soft low durometer rubber rim forming a skirt that deflects to open and spreads out under the effect of the downward vacuum force. This increases the surface contact area and improves the seal. This can be appreciated with reference to FIGS. 5A-5C. FIG. 5A shows the vacuum expander when not in contact with tissue (the skirt (rim) 102 is spaced from the tissue). When pressure is applied, the expander adapts/conforms to the complex surface contour of the body, absorbs to body movement by bending and deflects with increasing force to increase surface contact. This conformance can be seen when partial (mild) pressure is applied to expander 100 as skirt 102 spreads laterally outwardly and conforms to the skin surface S (FIG. 5B) and when full pressure is applied as shown in FIG. 5C, with increased surface area contact. The undersurface 102a of the rim (skirt) 102 better engages the skin as its shape changes as shown in FIG. 5C. Thus, with increasing downward force, the rim of the device deflects (i.e., moves laterally outwardly) to increase the surface contact and prevent an increase in counter pressure against the peripheral skin, i.e., keep pressure against the skin at safe levels. (Note the rubber rim is not adhesive and glides over the skin due to a lubricating layer as described in detail below). Furthermore, the deeply concave design/configuration of the skirt/rim forces its feathered-out periphery to grip down and espouse the complex convex surface contour of the torso to maintain the air-tight seal. This deflective conforming soft rubber skirt can also accommodate a significant amount of body motion without losing the vacuum seal.

Figures 6A, 6B:
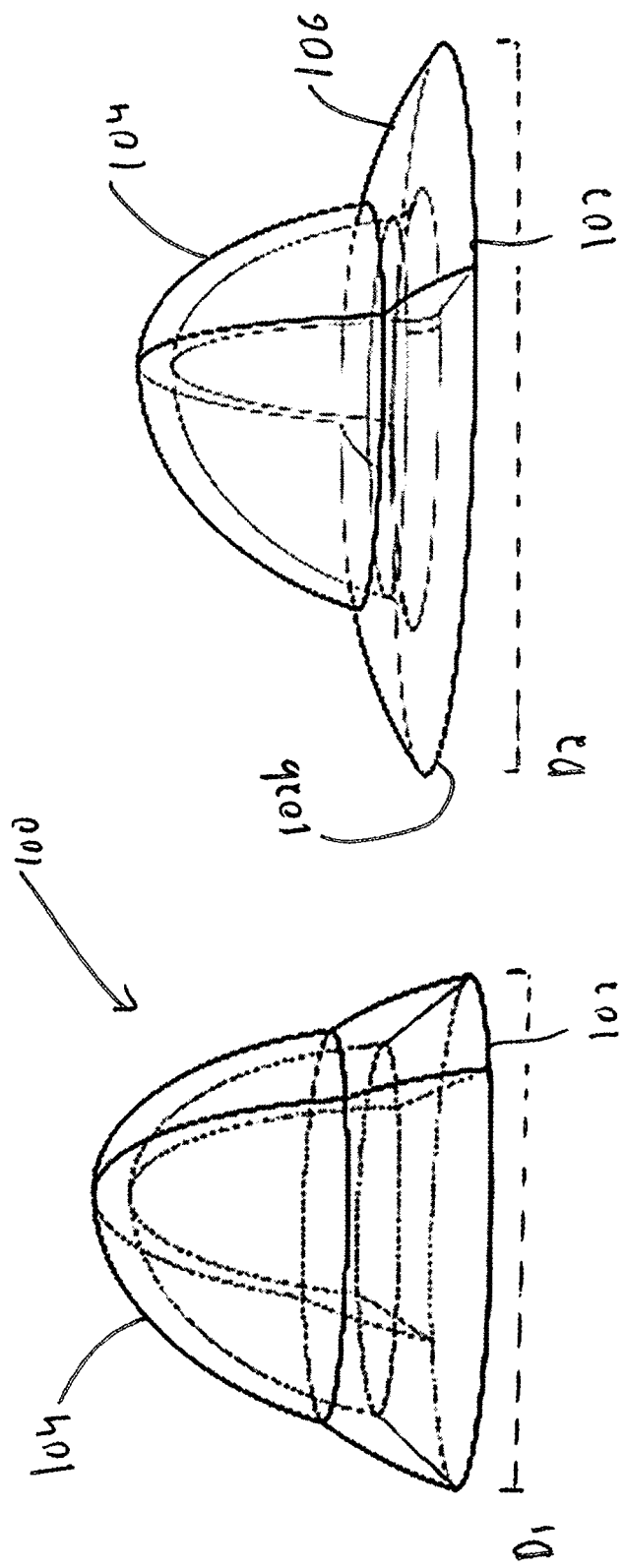
FIGS. 6A and 6B are perspective views of an embodiment of the vacuum expander of the present invention illustrating the rim skirt of the dome (shell) widening for adaptation to the complex convex contour of the torso.

A comparison of FIGS. 6A and 6B shows for illustrative purposes the widening (lateral outward spreading) of the skirt 102 when the dome 104 of the device 100 is forced downward on a flat surface by increased vacuum pressure. It is designed to bend and widen (deflect out) in order to increase the surface contact as the vacuum pressure increases (more downward force is applied). That is, when applied to the convexity of the chest, the peripheral rubber rim is under two forces: inwardly pulling from circumferential stretch and downward flexion arc from resistance to bending (see arrows of FIG. 6C). These forces combine to make the skirt edge 102b wrap around the chest, grip the torso and tightly espouse its complex surface contour. The inward camber 102b of the skirt periphery (see FIGS. 5C and 6B) improves the grip as the circumference stretches. FIG. 6A shows the skirt 102 extending from the dome 104 of the expander 100 prior to application of pressure; FIG. 6B shows the skirt 102 expanded upon application of pressure as the diameter/or transverse dimension D2 of the skirt 102 is greater than the diameter/transverse dimension D1 of FIG. 6A. A comparison of FIGS. 6D and 6E also show that when the dome is forced down on a flat surface, the rim skirt widens and its periphery is stretched.

Taking into account the elasticity of the rubber material, its thickness and taper angle, the mechanical properties of the rim are engineered such that by spreading and widening with increasing downward force it increases the skin contact area to maintain the surface counter pressure below damaging levels. Furthermore, the design also prevents pressure points and ensures an even pressure distribution along the contact area. That is, because the thinner more malleable edge deflects more while the thicker proximal part deflects less, a relatively constant downward force is maintained on the tissues along the width of the rim.

FIGS. 6F-6J illustrates the configuration of the device 100, with aperture 124 within the dome, shown from various angles—side, bottom, top, etc. The shape of the preferred configuration of the rim interface is a skirt as shown in FIGS. 5A-5C and 7A-7C. It is long (e.g., about 2 cm to about 5 cm medially to about 4 cm to about 9 cm laterally), although other dimensions are also contemplated, tapers down, cambers inwardly and is deeply concave, (e.g., its axis is less than 15° from the vertical axis X, although other angles are also contemplated). It has a non-adhesive, non-adherent, very low durometer rubber sole that espouses the body contour and is designed to increase surface contact with increasing pressure by deflecting out and spreading.

As shown in the Figures, the rim tapers in thickness with a maximum thickness at the top 107 (closer to the dome 104 where it is connected at region 108), e.g., approximately 1 inch, tapering to a maximum of a few millimeters for example at the periphery 109. In some embodiments, it tapers (narrows) down at region 114 to a thinner feather thickness having a feathered edge 116 at a distalmost edge. An inner thin and very compliant feather 112 can be provided for additional seal. This thin feathered inner lip 112 provides a wider and better seal. Other thicknesses along the various regions of the rim are also contemplated to absorb movements, prevent pressure points, and more evenly distribute the counter pressure against the skin.

Figure 6C:
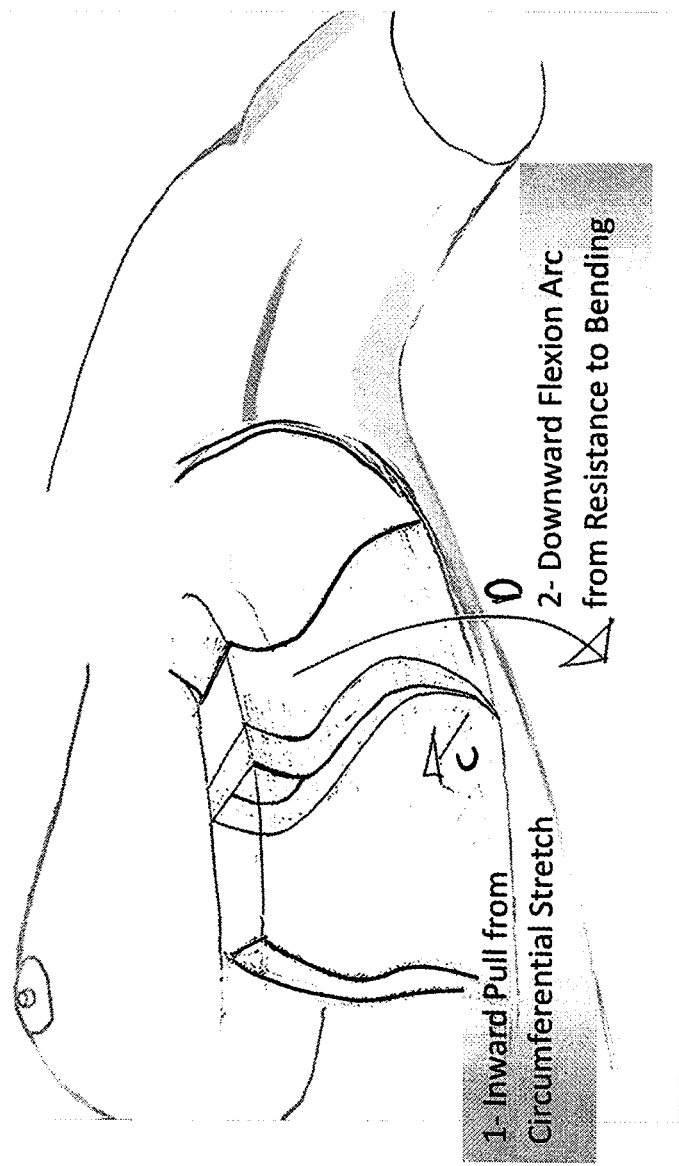
FIG. 6C illustrates the wrapping of the skirt of FIG. 6B when applied to the convexity of the torso.
Figure 6D:
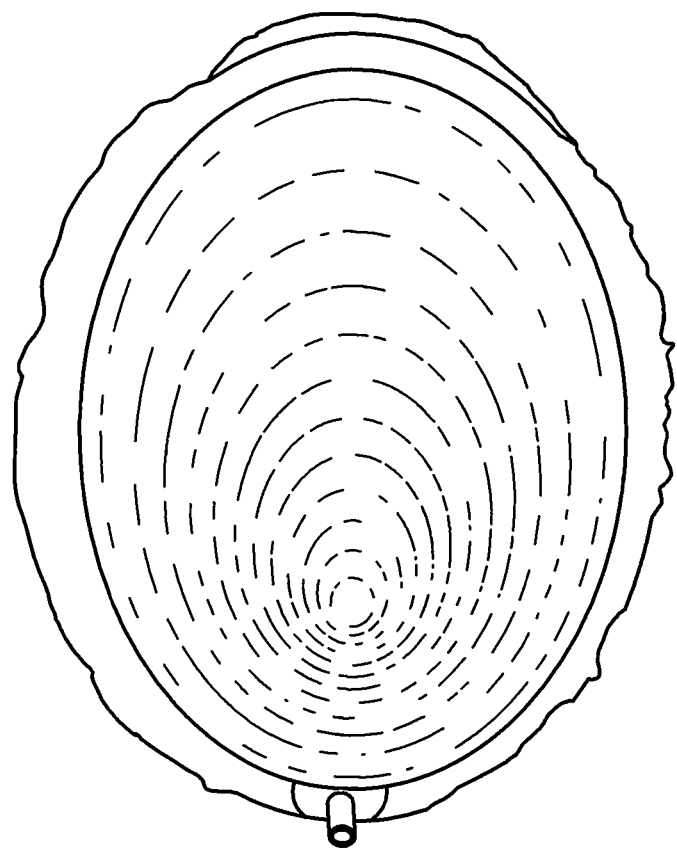
FIGS. 6D and 6E show how when the dome of the present invention is forced down on a flat surface (FIG. 6D), the rim skirt widens and its periphery is stretched (FIG. 6E)
Figure 6E:
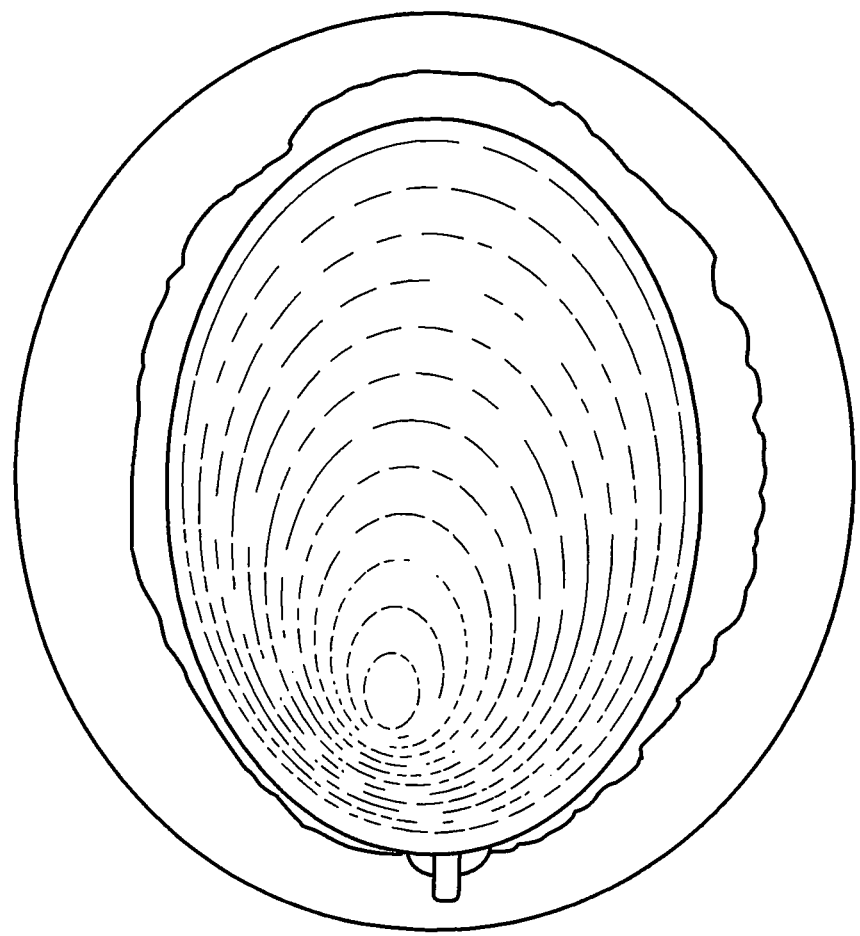

The rim is also in preferred embodiments an asymmetric design (see e.g., FIG. 6I), with a narrower (shorter) skirt 121 medially over the sternum and longer, more curved inward skirt 123 laterally to wrap around the torso. By way of example, it can have a long flange with a maximal length of about 3 inches on the lateral side, and minimal length of about 1 inch medially, although other dimensions are also contemplated. This asymmetric design provides the lateral side with a deeper concavity and longer than the medial side to wrap around the body contour. Note the thickness and length do not need to be uniform along the circumference as there is typically a left and a right side. The skirt rim 102 at rest (FIG. 7A), i.e., no contact of inner surface 102a with the skin, has a concave or straight down curve (see concave surface 103) in cross section with an inward camber 114 to force it further inward and grip the curvature of the torso as the periphery stretches out. The concavity becomes a convexity (see convex surface 105) where the downward force is highest under the harder rim and then feathers out as needed to even maintain some concavity at the very edge if needed to espouse the body contour. It angles significantly downward from the horizontal plane to form a long skirt-like rim. The downward angle could be constant or could vary. It typically can vary along the periphery. In preferred embodiments, the angle X from the horizontal is 45-85 degrees (or 45-5 degrees from the vertical), although other angles are also contemplated, thereby providing a large concavity depth. The skirt and its connection to the more rigid dome are designed such as when the vacuum pressure increases and the downward force increases, the angle X opens up and increases from near vertical to become more horizontal, and to keep the pressure even all around the periphery, it increase more on the shorter (narrower) medial side. The segment under the rim will change from concave to convex while the periphery, especially the lateral side, might need to remain concave to preserve seal as seen in FIG. 6C. Stated another way, the angle X varies from near vertical to 60 or near horizontal with application of pressure. Thus, when downward pressure is applied, a downward force from the dome is counteracted by the skin and the rim can stretch out to from a concave (lower surface) to a convex (lower surface) or near flat configuration at its highest pressure point while remaining concave at the lateral peripheral edge, and the counterforce between the skirt and tissue is evenly distributed over a contact area of the skin to avoid pressure points with increasing pressures.

The rim, with its deep concave shape, is preferably made of a low durometer synthetic rubber material such as silicone or newer formulations of urethane. With increasing pressure, the rim increases its deflection to increase the contact area and reduce the counter-pressure exerted on the skin. Furthermore, it is designed such that the applied vacuum does not cause it to buckle inward and get sucked into the dome section. (This would reduce the aperture of the expansion surface). In preferred embodiments, a low durometer (anywhere on the entire Shore 00 scale), or on the low shore A scale (less than 25 Shore A) rubber, preferably silicone or medical grade urethane is utilized. Such materials have the required softness (close to gel like) to be comfortable and elastic rigidity to properly deflect and evenly distribute the pressure as the rim which contours to the skin surface deflects with pressure. (While there are different overlapping shore scales, it is understood that any scale used would be specifying materials of similar and crucial mechanical property as the ones mentioned above. It should also be noted that these are novel materials not widely available until recently for medical use). However, different materials, and combination of materials of different durometers, are also contemplated. The rim material is stretchy enough (very low durometer rubber) so that when pressure is applied and the downward force from the dome is counteracted by the skin, the skirt can stretch out to a flat or near flattened shape. Though more complicated to manufacture, it is also contemplated in alternate embodiments to have the skirt made of varying durometers along its thickness and circumference in order to reduce bulk weight and make it more comfortable and concealable, provided the concavity, the taper angle, the width and the deflection property under downward pressure preserve adequate deflection under the physiologic pressures used to evenly distribute the pressure avoiding pressure points. That is, the softer durometer material is more comfortable and conforming against the skin, but is bulkier (thicker). (In some embodiments, the softer durometer can be like a gel). The higher durometer is thinner but less comfortable. Thus, in some embodiments, the durometer can vary so it is harder adjacent the center of the dome to provide reinforcement to hold it together and softer at the periphery for comfort and conformance. In some embodiments, the variable durometer concept can be utilized so that it progressively decreases in durometer toward the periphery. In such variable durometer embodiments, the delicate balance needs to be achieved between comfort/conformance and reinforcement.

Figure 8:
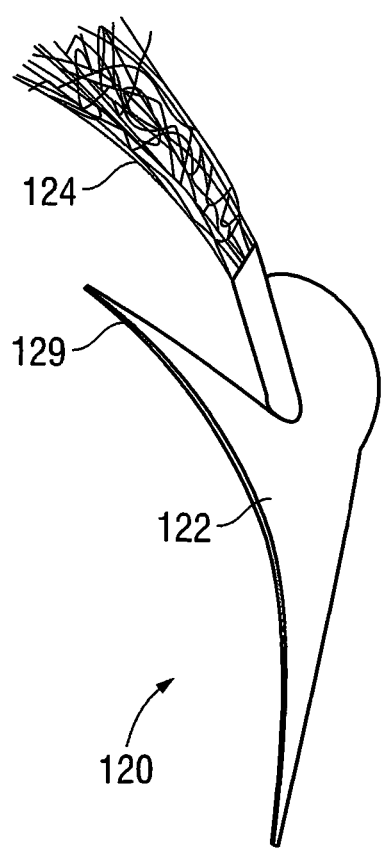
FIG. 8 is a view similar to FIG. 7A showing other depths of the dome shell attached to the rim and also showing an alternative rim design with an additional inner thin and compliant deflecting rim that increases the contact area against the skin to improve the vacuum seal.

The rim design variables include durometer of the material (e.g.,) rubber, its mechanical properties, its thickness, its rate (angle) of taper, its concavity, its length and its shape, and these variables are design engineered/optimized in order to increase surface contact with increases in vacuum pressure to decrease the counter pressure on the skin—as the skirt flattens with downward pressure, the counter force between the skirt and the tissue is evenly distributed all over and around the contact area. The above variables are design engineered such that there are no concentrated pressure points, but rather a distribution, preferably an even distribution, all over the skin contact area. The taper angle and concavity are also designed to evenly distribute pressure under the spread out skirt such to avoid pressure points. With increasing pressure, the rim increases its deflection, i.e., deflects out and widens, to increase the contact area and thereby reduce the counter-pressure exerted on the skin. The design leads to a near linear relation between vacuum pressure increases and surface contact area increase. To illustrate, when the vacuum pressure doubles, the rim flattens and spreads out to double the contact surface against the skin and keep the pressure it exerts against the skin low and even all around its circumference. This property of the concave tapered deflecting rubber sole that increases surface contact with increases in the downward force balances the forces to keep the skin pressure below damaging levels:

FIG. 8 is a view similar to FIG. 7A schematically showing other depths of the dome shell 124 attached to the rim 122 of expander 120 and also showing an alternative rim design with an additional inner thin and compliant deflecting rim 122 extending inside the dome aperture that increases the contact area against the skin to improve the vacuum seal. This thin inner rim is very soft and compliant, it is not designed to distribute the pressure but to improve the surface contact against the skin and therefore the seal. The rim can include a feathered region 124 similar to feathered region 112 of FIG. 7A. The domes 124 can be permanently attached or interchangeable as described below.

FIGS. 7A-7C illustrate the increased contact area as pressure increases. In FIG. 7A, the vacuum expander 100 of the present invention is shown with inner/lower surface 102a of rim 102 not in contact with tissue. The long, tapered low durometer rubber rim and the near vertical axis of the rim skirt in this no-contact position are illustrated. As shown, the concave configuration 114 cambers inwardly to hug the chest contour and prevents the edges from flipping up under elastic recoil as the perimeter increases with increasing elastic stretch. The cambered inward curvature forces the periphery to hug tissues down with increasing stretch. Under low pressure (arrow C of FIG. 7B), as it gradually opens up, the rim 102 deflects (see region 118) and conforms to the skin surface (breast edge and curved chest contour). As the downward force increases under higher pressure (arrow D of Figure C), it fully opens as the rubber rim 102 bends outward and spreads out to increase surface contact (FIG. 7C) and keep the pressure against the skin at safe levels. The edge wraps at periphery 109 around to conform to the body contour.

Figure 9A:
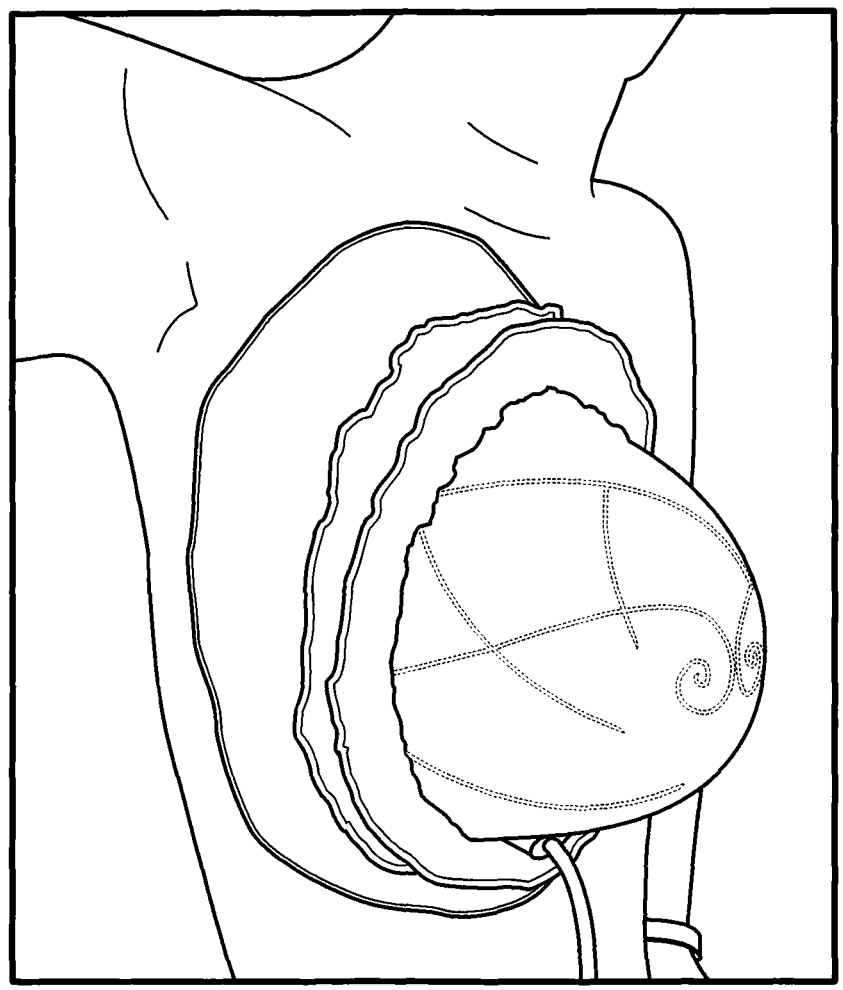
Figure 9B:
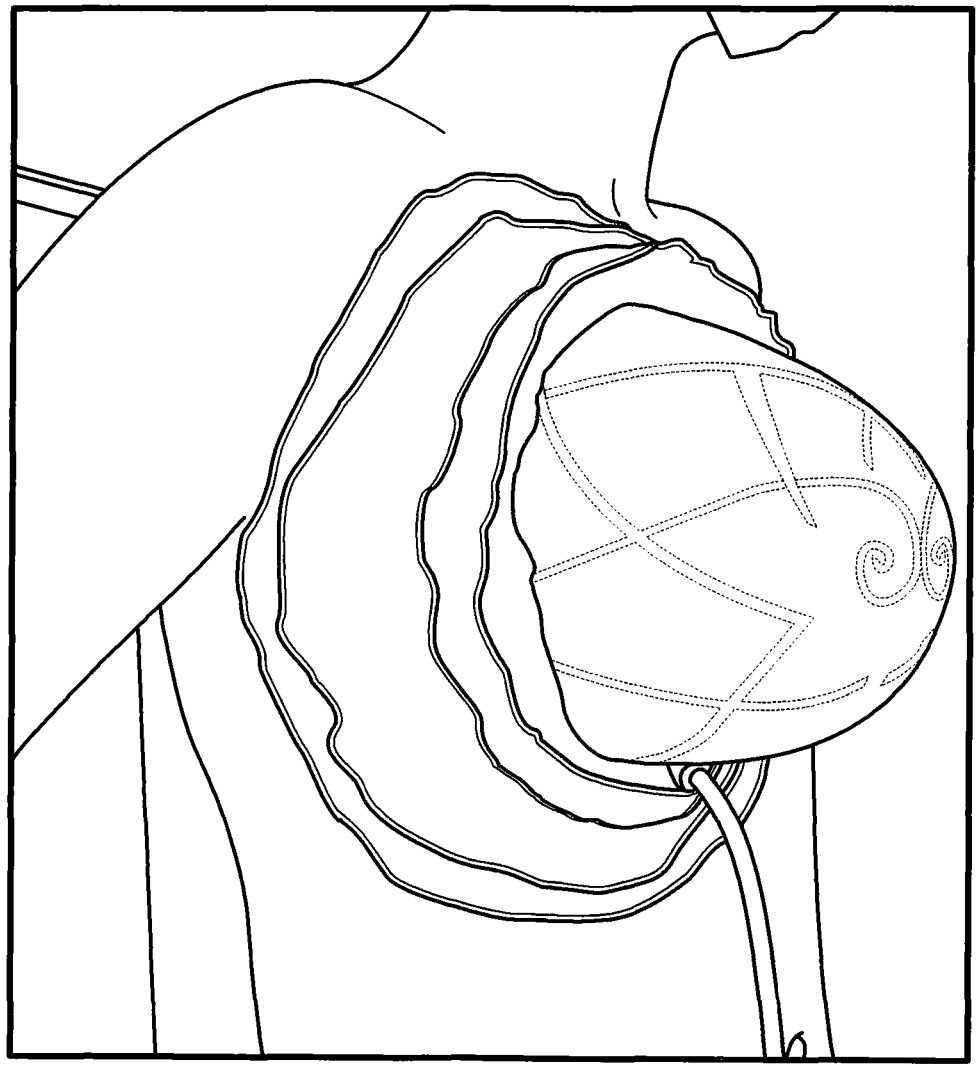
Figure 9C:
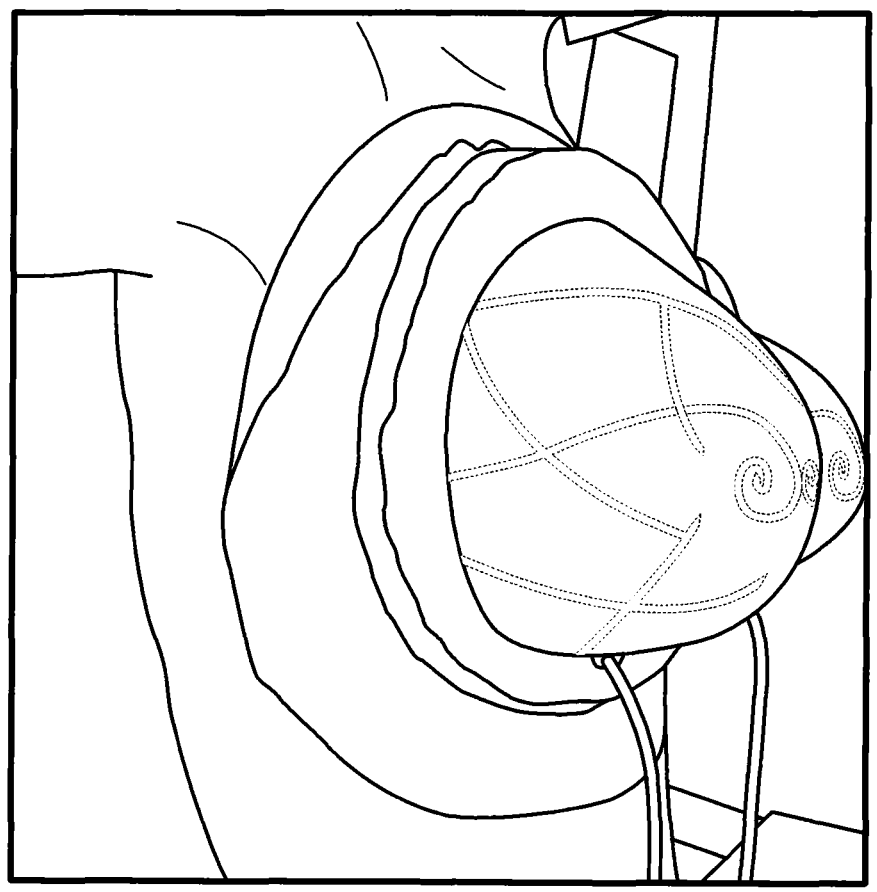
FIGS. 9C and 9D show how the thin feathered edges might tend to roll up from tension around the periphery and the edges do not wrap around to follow the chest contour in the absence of the fins of the device of FIG. 9A.
Figure 9D:
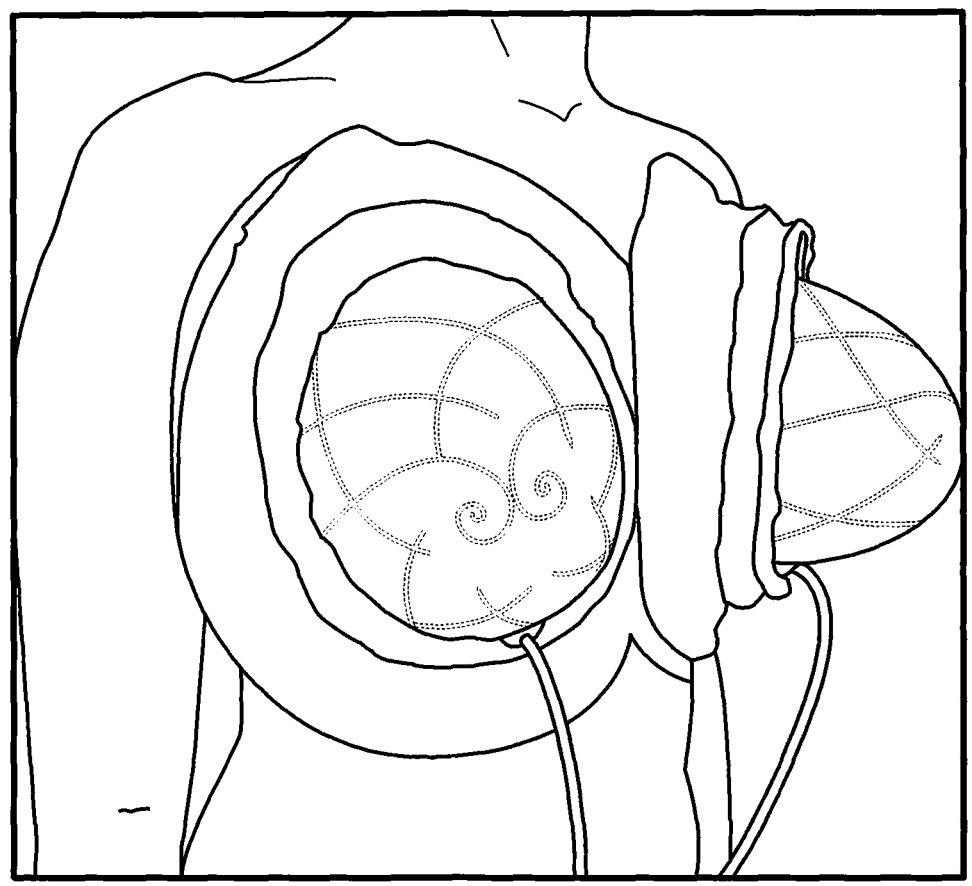

A thin feathered inner rim (feathered lip) to increase contact area and improve the seal could be provided, as illustrated in FIGS. 7A-7C and 11. In some embodiments, as shown in the expander 140 of FIG. 11, a fin pocket 142 or slit can be provided to insert fins 144 to follow the convexity of the chest contour. The fin 144 can be reshapeable and repositioned along the perimeter of the rim to best follow the chest surface contour. The fin pocket 142 in some embodiments could address the issue of the skirt folding up and out under the effect of the peripheral tension and not adequately wrapping around the torso at the lateral chest border as shown in FIGS. 9C and 9D. By providing the fins that curve inwardly and are feathered in configuration, there is less inward force at the tip (see FIGS. 9A and 9B). Expander 140 can also have an inner feathered lip 143 for an additional seal. The concave shape 148 and feathered edge 150 of rim 146 better conform to the torso as described herein. The non-adhesive tapered soft rubber sole 146 deflects outward with pressure as in the embodiment of FIG. 7A-7C. The dome 134 is attached to rim 146, and has peripheral edge 136. Furthermore, in some embodiments the fins can be a permanent component of the skirt. The dome shell might include a thickened rim or a cane handle design at its periphery to increase surface contact against the soft skirt and prevent it from cutting into it.

Figure 1C:
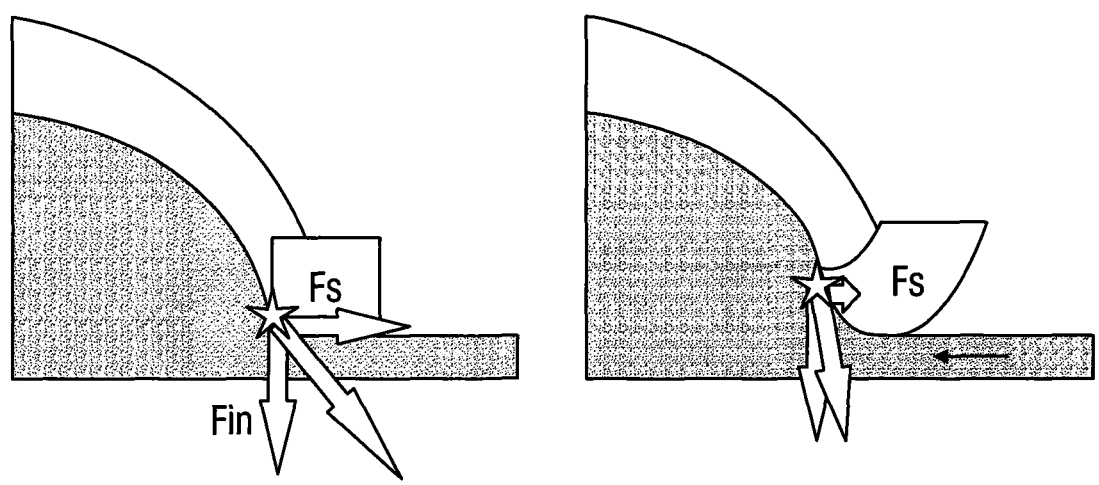
FIG. 1C is a schematic view of the shear effect during use of an external vacuum expander of the prior art.

With respect to shear stresses (challenge #3), the above vacuum expanders of the present invention completely solve the shear stress problem. The forces and shear effect can be appreciated with reference to FIG. 1C and are also described in U.S. Pat. No. 6,500,112 (same inventor as the present invention). (The entire contents of U.S. Pat. No. 6,500,112 are incorporated herein by reference). The objective is balancing counter pressure and reducing skin shear stress as described in the '112 patent. FIG. 1C shows the inward deflection of the adhesive gel rim of the prior art Brava device to dissipate shear forces with the drawing on the left showing the shear effect and the drawing on the right showing the reduction of shear stresses due to the inwardly deflecting adhesive rim (sole).

In the present invention, a soft rubber rim instead of an adhesive rim is provided. The soft rubber rim maintains a vacuum seal by faithfully espousing the body contour so there is no need for an adhesive layer (or other skin-adherent layer) so the rim is thus non-fixedly/non-adherently/non-adheredly positionable on the skin of the patient to enable sliding outwardly. The device rim (skirt) can have a lubricant or other material to provide near friction free gliding between the skin and the skirt that opens to wrap around the body. With the contact surface no longer glued and anchored to the rim as in devices using adhesive (or other adherent material or structure) which fix the position of the rim and device, the skin is free to move, and the tension can recruit as much peripheral skin as necessary to dissipate the damaging shear stress. With this near free tissue recruitment there is lower strain, lower force, and lower shear stress.

Thus, the vacuum expanders of certain embodiments of the present invention have a lubricated skin-to-rim sole contact area to allow a friction free skin recruitment (and sliding/gliding) that dissipates the shear forces. The lubrication reduces shear stress between the contact surfaces of the skin and the device. In the prior art, the skin is anchored to the contact surface via high friction interfaces or more frequently via adhesives. Lubrication of the present invention takes away this anchoring and thus removes or reduces the shear force.

The lubricant or a low friction film can be applied in one or more of the following ways: a) applied to the skin before placing the device on the skin; b) applied to the bottom (lower) surface (sole) of the rim itself before placing it on the skin and/or c) be in the material of the rim so that it continually lubricates. (The bottom (lower) surface refers to the surface closer to the breast tissue, and is also referred to herein as the sole or base). The lubricant or low friction film can be added separately, or alternatively, the rim sole material can have an inherently low friction coefficient thus removing the need for lubricant or film. Thus, the device is non-adhesive/non-adherent to the skin and has a low friction contact skin surface either inherent or by the addition of a lubricant or film interface. Such lubricants which can be utilized to remove or reduce the shear forces between the skin and the device contact surface (rim) include by way of example, grease, petroleum jelly, oils, waxes, KY Jelly, glycerin, hydroxyethyl cellulose, water, liquid, jell, cream, or wax of any type, an Allergen free lubricating material with excellent skin tolerance such as cocoa butter, petrolatum gel, Vaseline, Nivea, Aloe Vera, mineral oil, etc., or a combination of these.

Figure 4:
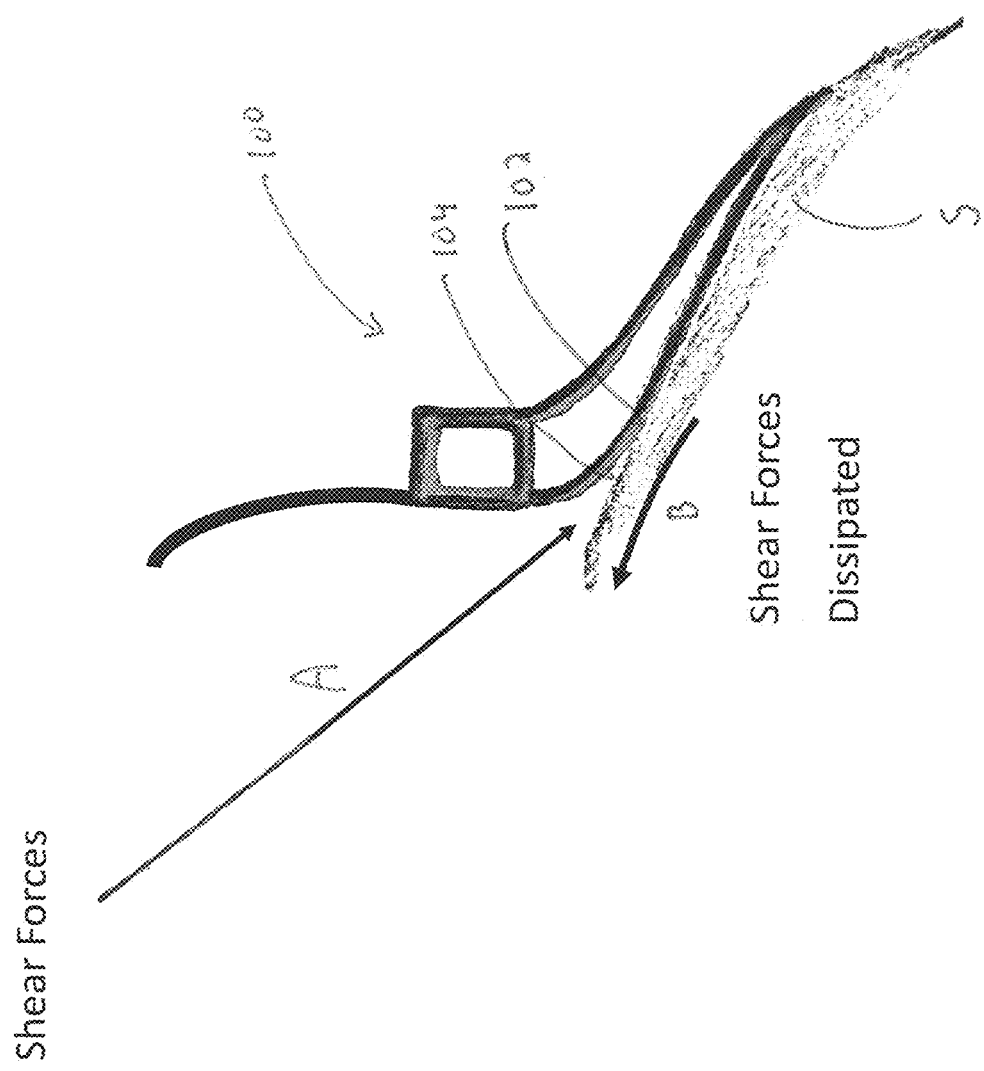
FIG. 4 is a schematic side view of the external vacuum expander of an embodiment the present invention shown in contact with breast tissue, the arrows indicating the shear forces that are dissipated due to gliding of the dome.

FIG. 4 illustrates damaging shear forces (arrow A) created when the vacuum inside the dome pulls inward the skin held under the rim. The rubber rim of the present invention is non-sticky and allows free skin gliding and has a low friction coefficient against the skin (either inherent in the material or via application of lubricant on the skin or rim sole). As shown by arrow B in FIG. 4, the shear forces are dissipated due to the gliding of the lubricating layer that allows inward skin recruitment.

Figure 2A:
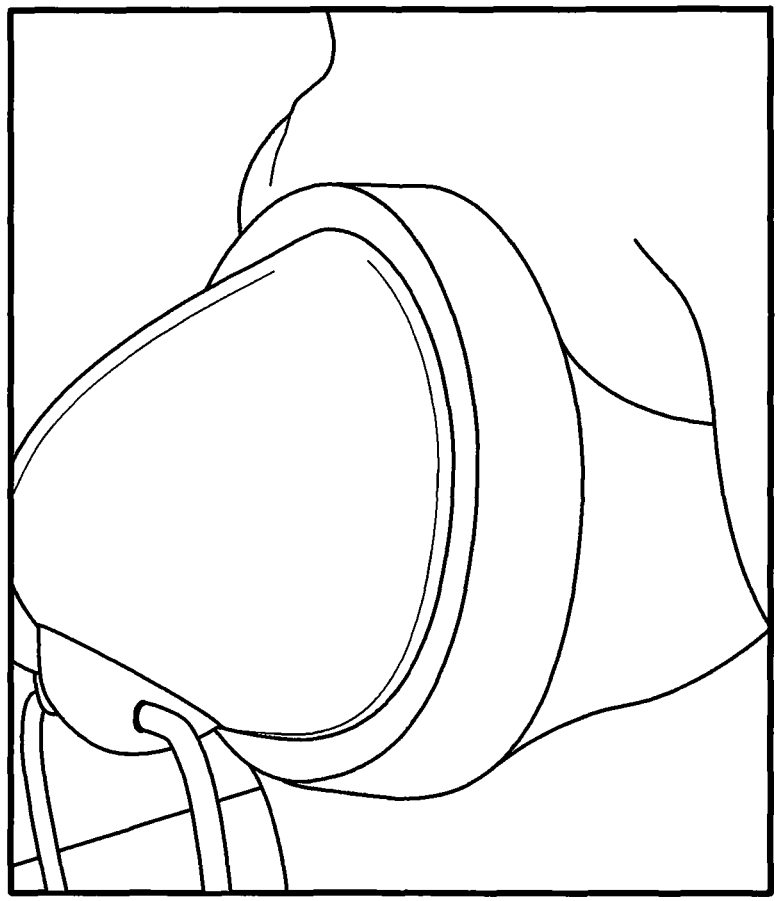
FIGS. 2A and 2B show how the vacuum applied to the device of the prior art with an adhesive gel rim squeezes the breast like a vise as the rim deflects inwardly to dissipate the shear stress with FIG. 2A showing no vacuum and FIG. 2B showing applied vacuum.
Figure 2B:
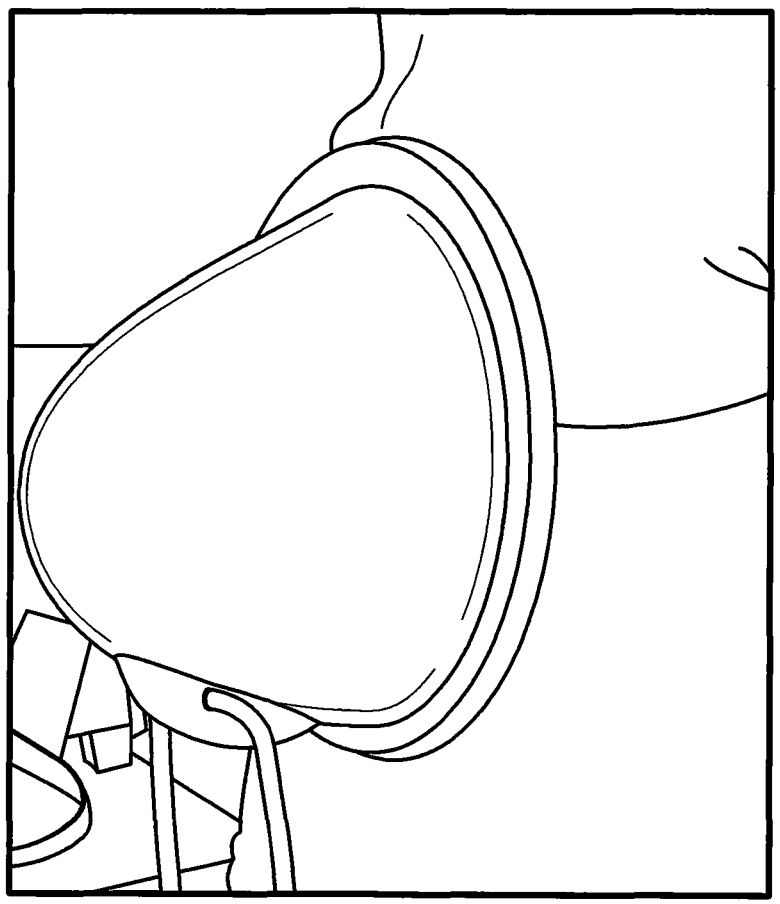
Figure 2C:
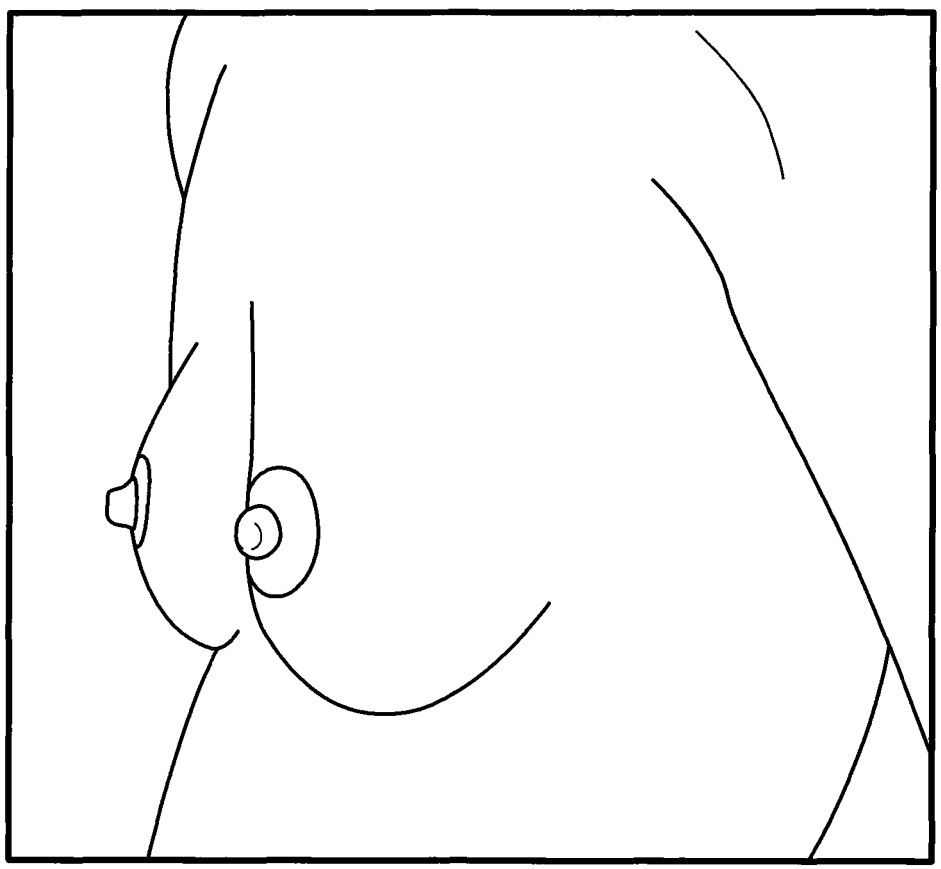
FIG. 2C shows how limited inward deflection of the adhesive rim of the prior art such as the device of FIG. 2A causes skin damage from shear forces.

The limited deflection under higher pressure of the adhesive rim of the prior art can be appreciated by the photographs in FIGS. 2A and 2B showing no vacuum in FIG. 2A and application of vacuum in FIG. 2B. With higher pressure, the adhesive rim deflects inwardly and fails to dissipate additional shear forces, reduces the aperture expansion area and squeezes the breast like a vise. The high pressure can also delaminate and destroy the silicone gel rim. FIG. 2C illustrates an example of how limited inward deflection of the adhesive rim of the prior art can cause skin damage from the shear forces.

Examples of the shear effect in a small and large dome (shell) of the prior art, illustrating how a larger aperture pulling on a larger surface will tend to create more inward pull and therefore more shear force concentrated at the rim that can damage the skin are depicted in FIGS. 3A and 3B. As shown, rims 11a, 11b are attached to domes 10a, 10b, respectively, positioned on skin S. When suction (vacuum) is applied to a small dome 10a (FIG. 3A), the shell (dome) moves from a flat to a dome shape, and 3 cm of skin (breast width) will elongate 10% (3 mm). When suction (vacuum) is applied to a large dome 11b (FIG. 3B), the shell (dome) moves from a flat shape to a dome shape, and 12 cm of skin (breast width) will elongate 10% (1.2 cm). If the rim is held firmly at the edges, i.e., by the adhesive of the prior art, the 1.2 cm causes higher shear that cannot be accommodated and the skin will tear. The devices of the present invention prevent this by, as discussed above, 1) enabling the rim to deflect inwardly; 2) having a lubricated interface to freely recruit peripheral skin; and 3) having a friction fee recruitment of the non-adherent rim base.

The vacuum expanders of the present invention in preferred embodiments have a portable vacuum pump with a pressure control mechanism. However, in alternate embodiments, a manual pump such as a bulb can be utilized. With manual pumps, a pressure relief valve can be included to prevent vacuum pressure from reaching damaging levels.

The devices of the present invention can alternatively function without a pump since surface tension is not required. In such embodiments, the vacuum source is the elastic recoil of the rubber sole. The device is placed over the breast and the air is "burped" out until the rim flattens down completely. At that point, the vacuum pressure inside the dome is a function of the elastic recoil force of the rubber and the surface aperture area of the dome. (Pressure=Force/Surface area). Given a fixed surface of the breast, the rubber sole shape design and its modulus of elasticity determine the force required to maintain the pressure within safe therapeutic range. A relief valve could also be included for added safety. Stated another way, the device would use surface tension in the dome section of the device to adhere to the skin so an active vacuum is not needed. The concept is to burp the air out of the flexible dome and rely on the natural recoil of the dome and/or dome rim to pull on the breast tissue.

In some embodiments, a special garment bra can hold the device in place. This can offer the same effect as pressing the feathered edge of the skirt to fold down and wrap around the chest contour to maintain the seal. The bra has first and second apertures or openings that hold the rubber rim and the dome. This component secures the device as the non-sticky device would otherwise fall off whenever the pressure abates. The bra can have a special design to include a series of reinforcement straps and/or padding cushions that maintain the loose feathered peripheral edges of the skirt in firm contact with the skin all around the breast in order to ensure the vacuum seal. The bra hugs the body contour to force the feathered edges to stay in contact with the skin. Reinforcing bands can connect the bra to the rim.

In some embodiments, a tapered thin additional inner rim that blends with the outer rim to increase the sealing surface without interfering with the vacuum expansion force can be provided.

Figure 11:
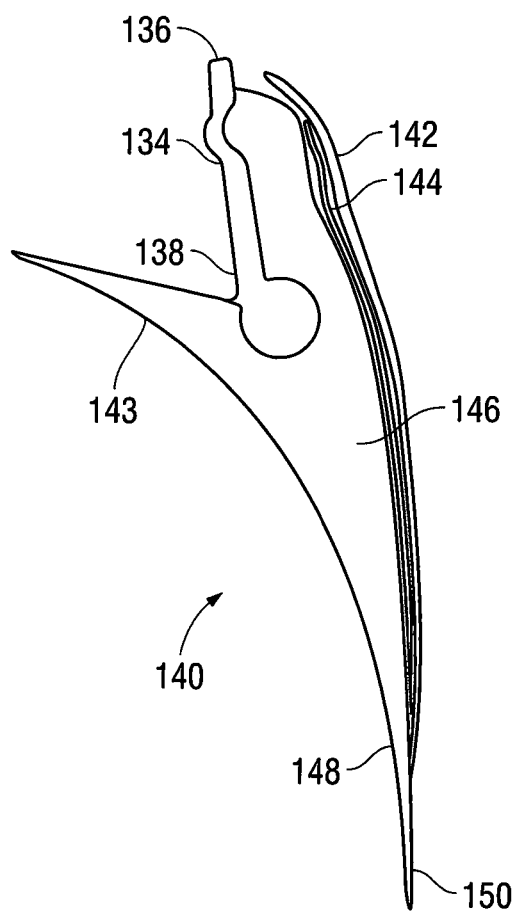
FIG. 11 is a schematic view of an alternate embodiment of the vacuum expander of the present invention having an inner feathered lip and pockets/slits to insert reshapeable fins to follow the convexity of the chest contour.
Figure 12:
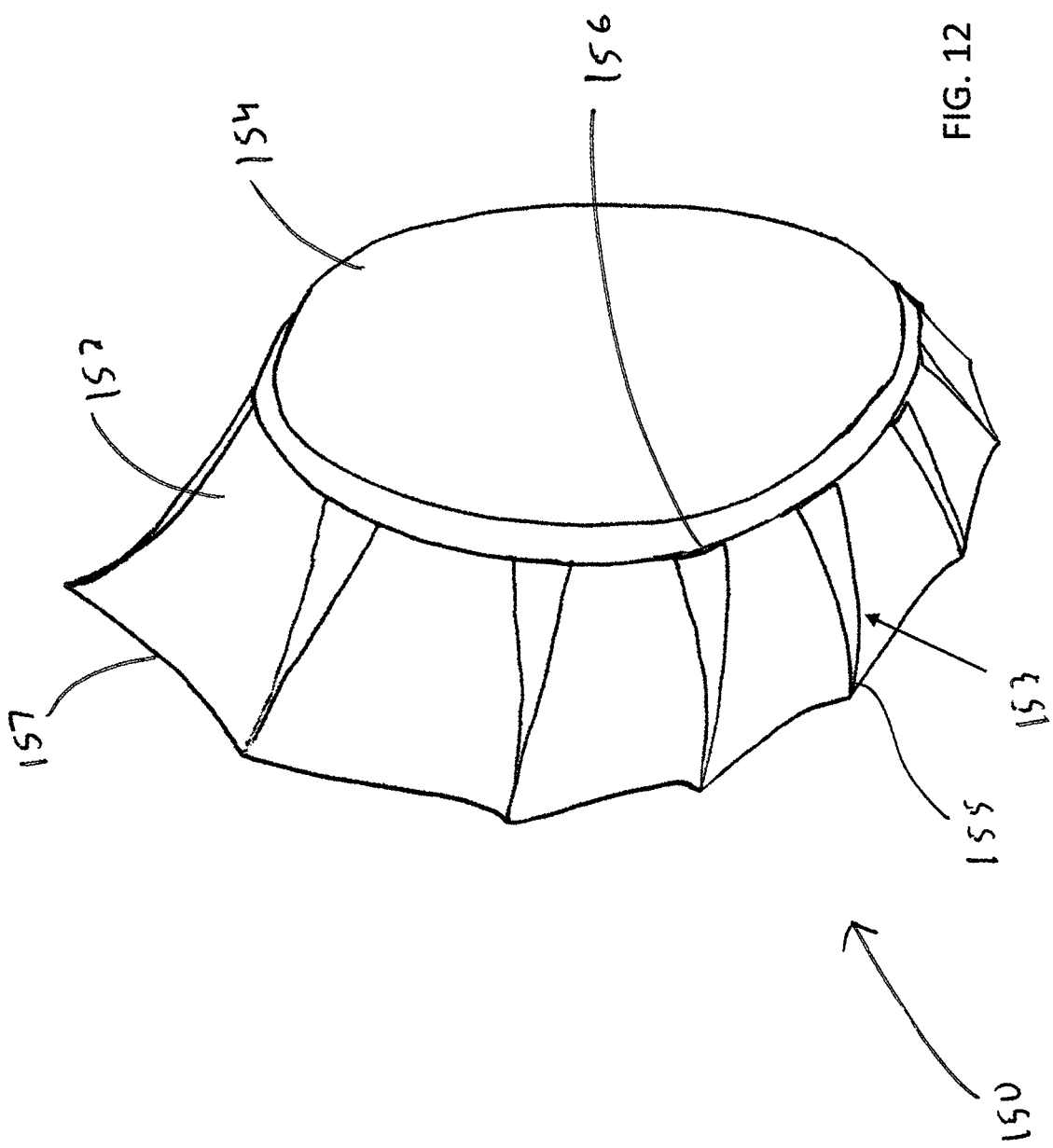
FIG. 12 is a schematic view of an alternate embodiment of the vacuum expander of the present invention having thin tapered fins with arcuate notches between the fins to prevent roll up eversion.

In some embodiments, the rim is radially reinforced with a series of adjustable thin tapered concave fins to better hug the body contour. FIGS. 9C and 9D are drawings showing how the thin feathered edges of the rim could in certain applications roll up from tension around the periphery and the edges not wrapping around to follow the chest contour; FIGS. 9A and 9B are photographs showing how the rim of the vacuum expander of the present invention is shaped to wrap around the chest and hug the skin surface contour to avoid the pitfalls of the expander of FIGS. 9C and 9D. The rubber rim, in these alternate embodiments of FIGS. 9A and 9B, has thin tapered fin-like inward cambered ribs to wrap around the chest and hug the skin surface contour. The ribs can be inserted inside pre-formed pockets at the outside surface of the skirt to provide additional inward camber if desirable. The ribs can be provided at select locations where they are needed to best espouse the patient's particular chest wall surface topography. The rim can also have arcuate notches between the fins to prevent its eversion as the periphery stretches with increasing surface contact. An example of an expander with tapered fins is shown in the embodiment of FIG. 12 wherein the fin 153 extends from the peripheral edge 156 of dome 154 to the end 155 at edge 157 of skirt 152. FIG. 11 also shows a fin 134 to reinforce the rim 146 extending to a peripheral edge 136 of the dome shell.

Figure 6F:
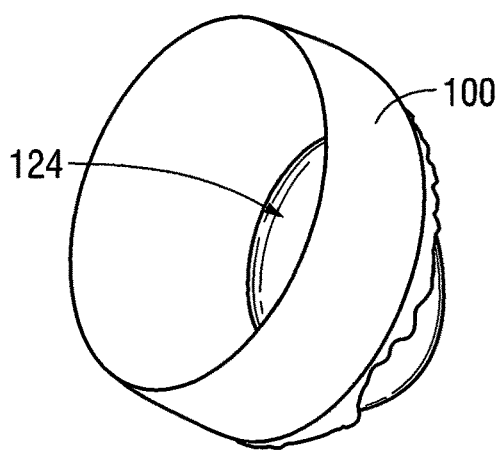
FIGS. 6F-6J show various views of an embodiment of an asymmetric dome of the present invention.
Figure 6G:
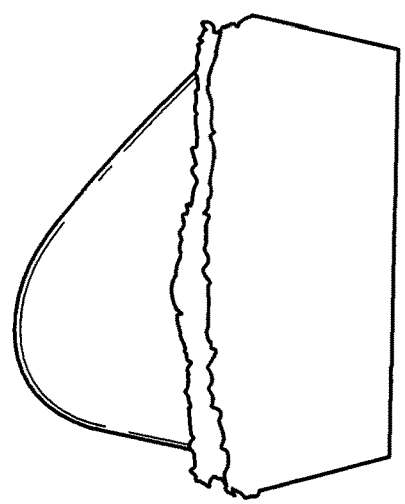
Figure 6H:
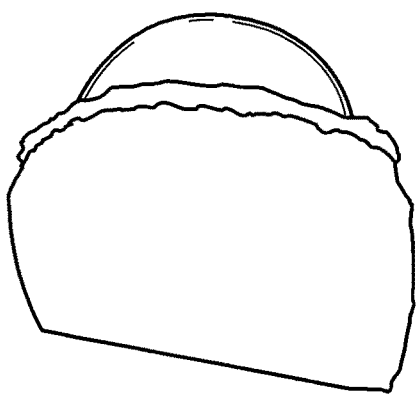
Figure 6I:
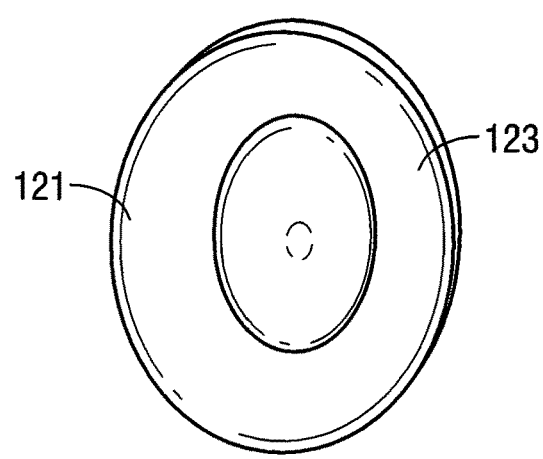
Figure 6J:
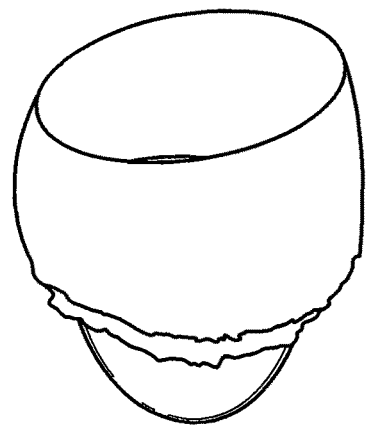

FIG. 6F also shows the left/right asymmetry of the rim as in the aforedescribed embodiments with more length laterally to conform to the lateral chest, a shorter medial length over the sternum to limit medial overlap and a deeper angle laterally to hug the side of the chest. The ribs/fins placement, curvature and length can be adjusted to fit individual patients, i.e., fitted with ribs/fins of different size, camber, stiffness, etc. where necessary along the circumference of the rim to achieve the best air tight fit based on the patient's torso contour. The photographs of FIG. 6F shows various views of an embodiment of an asymmetric dome of the present invention, Note the asymmetry in length and curvature between the medial and the lateral sides of the dome skirt. Also note the length, the near vertical design and the gently inward curved feathered edge.

In some embodiments, the rim can have an arcuate periphery that spikes at the reinforcing rims and is concave in between (duck feet).

In some embodiments, ribs of varying curvature and length judiciously inserted inside the rubber skirt at various points within its periphery can help it better adapt to the potentially complex and variable surface contour. Edges of the rim can also have an arcuate periphery with peaks at the site of the reinforcing ribs. A variable durometer construct, such as described herein, could also produce the same effect without the additional bulk.

Figure 10:
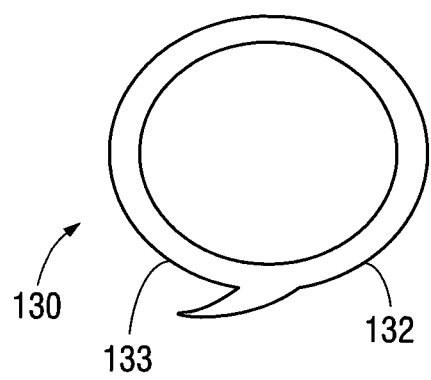
FIG. 10 is a schematic view of an alternate embodiment of the vacuum expander of the present invention having one embodiment of a tightening mechanism to secure the flexible rim to interchangeable harder shells.

In some embodiments, interchangeable breast shaped dome shells can be provided. A connector mechanism such as circumferential clasping/tightening mechanism 132 can be provided to secure the rubber sole (rim) 132 to the interchangeable shells (FIG. 10) and allow for easy removal and replacement with the selected dome. It should also be noted that the design and the circumference of the rubber skirt is slightly smaller than the circumference of the harder shell dome at their connection areas and configured such that the stretch of the rubber skirt in itself already provides an intrinsic lock and seal similar to the Tupperware seal of food items. That is, using for example a thick rubber band or an elastic string with an easy snap-tightened or spring lock tightened connection between the silicone rim skirt and dome, domes of various depths can be provided. In use, the connector mechanism is released, one dome is removed and a larger dome is secured to the rim by the connection mechanism. This allows the wearer to use the smallest, most innocuous (most concealable) to wear dome that still provides 1-2 cm of room for expansion. Once the breast expands to fill that small dome, the user can easily switch to a slightly larger one keeping the device worn as concealed as possible which is beneficial since the device should be worn near continuously.

It is also contemplated to have markers on the dome and/or on the skirt that need to match so when the dome is removed and replaced, the patient, properly connects a new dome, e.g., easily matches the top with the bottom and the left with the right to preserve the desired asymmetric configuration. This can ensure that the domes are replaced in the proper orientation (especially if the same molds are used for the right and the left domes and skirts).

Figure 13:
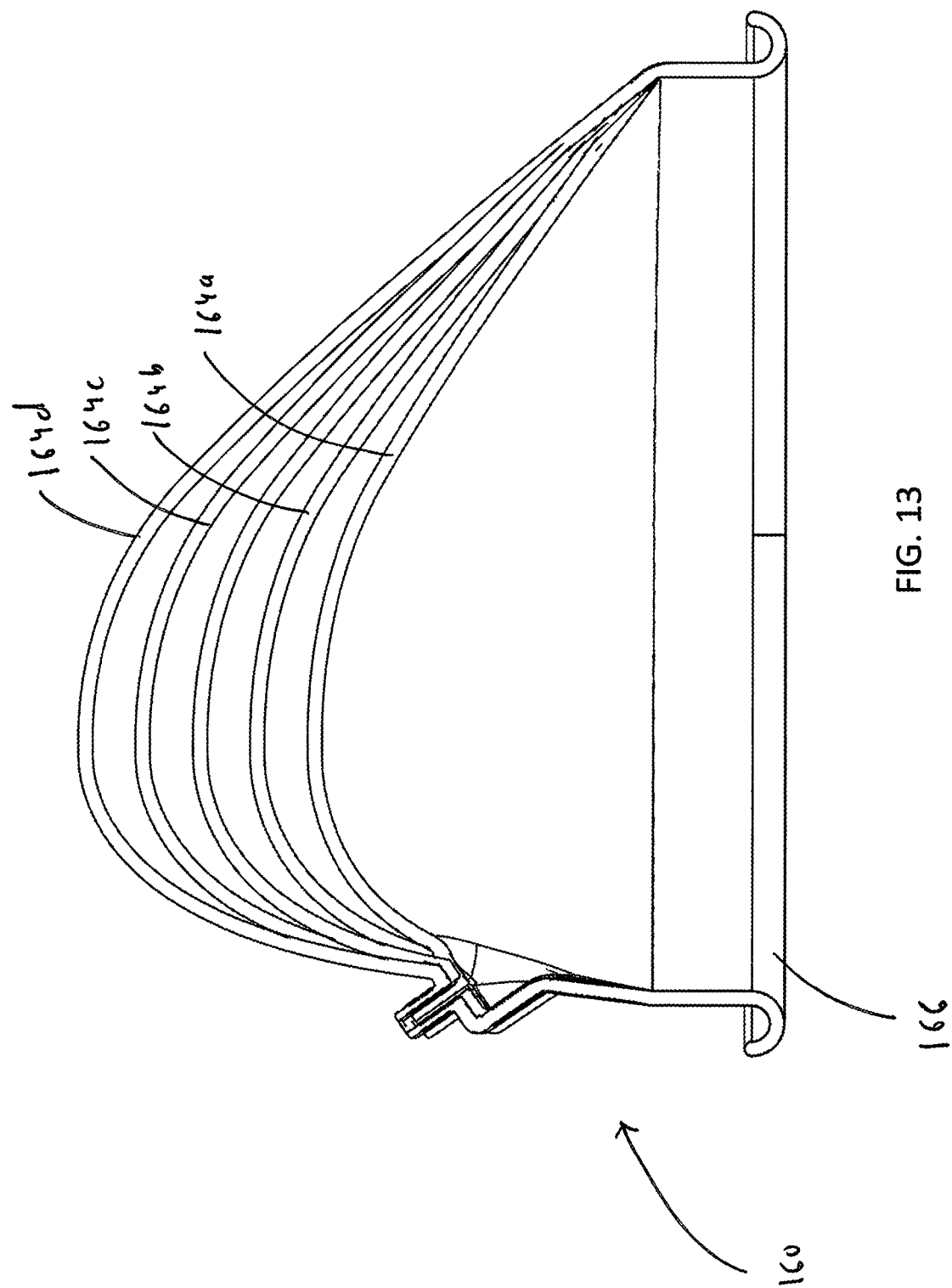
FIG. 13 is a side view showing an alternate embodiment of the expander of the present invention having different depths shell domes with a constant base to interface with the rim skirt.

The multiple depths of the dome shells, e.g., from an AA bra cup to a DDD bra cup, are shown in FIG. 13. The domes of different depths are attached to a constant base to interface with the rim skirt. Examples of various sized domes, e.g., 164a, 164b, 164c and 164d, are all shown attached to the base in FIG. 13 for illustrative purposes as it should be understood that one dome at a time (progressively increasing in size as the breast expands over time) would be attached to the base/rim. Additional or fewer number of domes could be provided. The device can be sold as a kit having multiples size depth domes detached from the rim for selective attachment by the clinician or the patient as needed to best fit as the breast expands. The device can alternatively be sold as a kit with multiple size/depth domes all permanently connected to their rubber rim. With these domes of progressively deeper sizes, it would allow the wearer to use the smallest, easiest to conceal dome, and move to the next larger size once her breasts fill that dome.

To be effective, the device of the present invention needs to be worn nearly 24/7. Therefore, it is preferable to be as concealable as a padded bra as well as be able to be worn as easily as their regular padded bra. It preferably should not add more than 1-2 cm beyond the original breast projection. It is therefore advantageous to have the smallest dome possible that still leaves room for the vacuum expansion. Once she fills the dome, she graduates to the next incremental size, either by selecting the next dome/rim or by removing the dome and attaching a larger dome to the same base (rim) in the replaceable dome embodiments. (FIG. 13 shows different size domes to illustrate the comparison of different size domes connected to the rim).

Figure 14B:
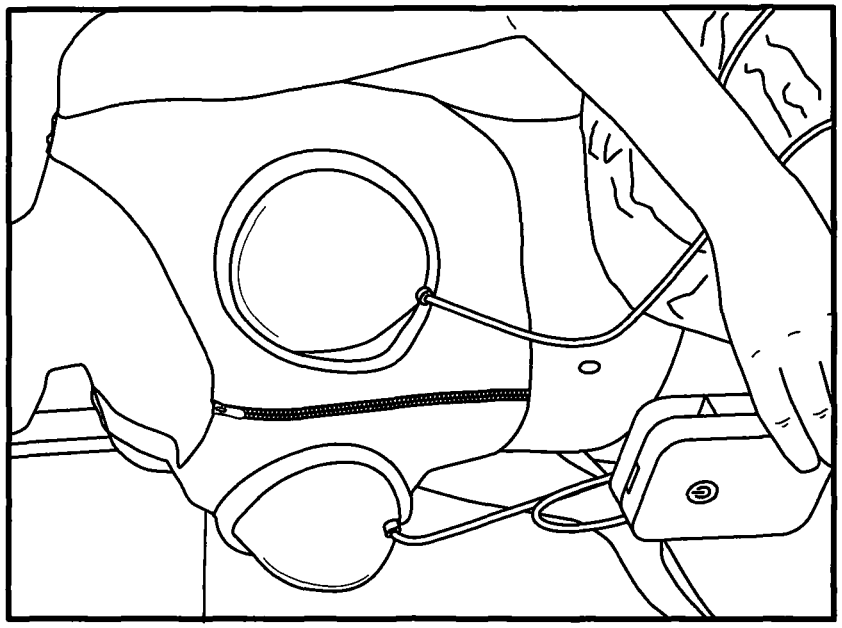
FIGS. 14A and 14B illustrate a mastectomy patient wearing a bra incorporating an embodiment of the vacuum expander of the present invention and holding a small pump.
Figure 14A:
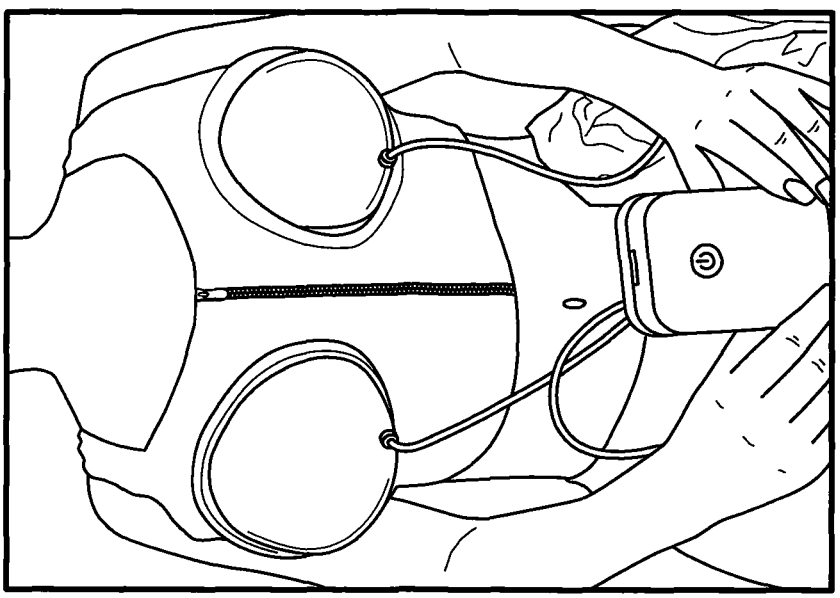
Figure 14D:
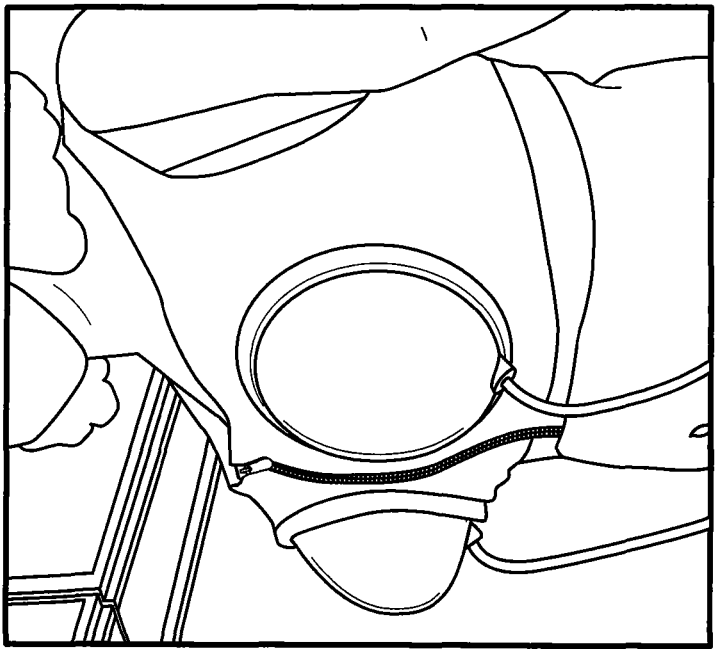
FIGS. 14C and 14D illustrate a cosmetic augmentation patient wearing a bra incorporating an embodiment of the vacuum expander of the present invention.
Figure 14C:
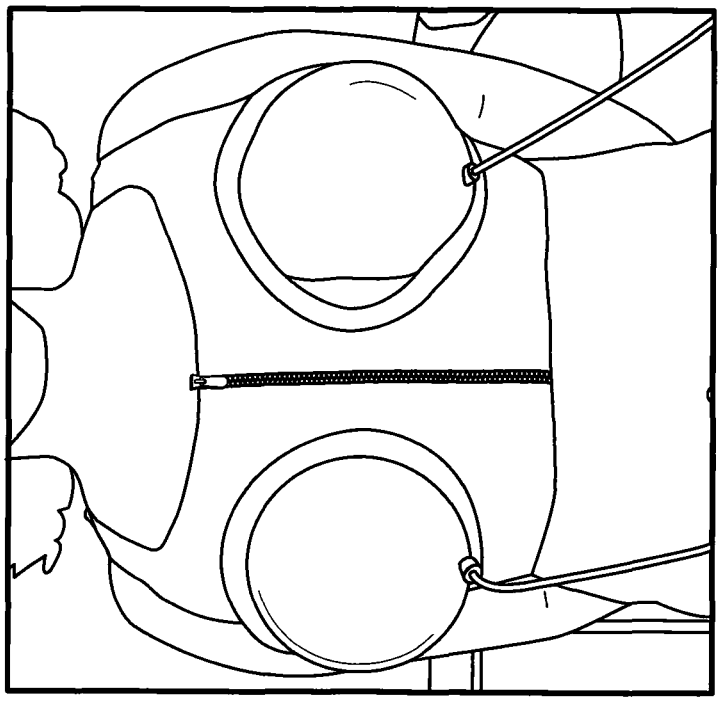

FIGS. 14A-14D illustrate an example of the expander of the present invention incorporated into a brassiere with FIGS. 14A and 14B illustrating a mastectomy patient wearing the bra and holding the small pump of the present invention for applying vacuum for expansion and FIGS. 14C and 14D illustrating a cosmetic augmentation patient wearing a bra of the present invention which is also used in conjunction with the small pump of FIG. 14A. As shown, the apertures in the brassiere each receive the dome and/or rim for placement on the skin. The dome and/or rim can be attached to the bra such that the inner volume of the dome is in communication with the aperture. The tubes connect the vacuum to the interior of the dome via an opening in the dome. The bra can include the reinforcements discussed above.

The dome is one shell shape that can be used as other shaped shells can also be utilized. Note the various shell and rim materials and structures/features disclosed herein be utilized for the shells of the brassiere, including the replaceable shell versions.

In preferred embodiments, the dome is made of transparent plastic and is translucent enough to visualize the expansion space between the nipple and the peak of the dome. The dome section can be permanently attached to the skirt by glue, sonic welding, or can cure with the skirt in a complex mold with potentially different rubbers. In alternate embodiments, the dome section of the device can be a separate plastic or rubber component that can be attached to and removed from the rim skirt.

The rigid shell is discussed herein and illustrated as dome shaped, however, it is not limited to such shape as it can be other shapes such as a cube, cylinder, etc. for forming the vacuum chamber, since pressure is isotropic. Thus, the discussion herein of shells utilizing the term "dome" is fully applicable to shells of non-dome shapes.

The dome (shell) and rim/skirt separation/distinction should be appreciated. If the skirt/rim is composed of rubber, there could be a gradual change in durometer from the skirt to the dome. Alternatively, or in addition, the dome can be rigidified with reinforcing ribs. There could be a skin, sheet, etc. covering both the dome and the skirt. The skin, sheet, etc. could be a hard-protective durometer or a soft-cushioning durometer.

It should be appreciated that materials other than rubber could be utilized for the rim (and other components/features) and are within the scope of the present invention.

The present invention could be used in combination with the surface tension concept of U.S. Pat. No. 10,433,947 if a rubber dome is used. In this combined embodiment, the wearer would need to find the proper dome size that perfectly encloses her breast. With no vacuum space, and with the skin in complete contact with the inner surface of the dome, surface tension between the dome and the skin would maintain a friction free adhesion. The air would be burped out of the flexible dome and rely on the natural recoil of the dome and or dome rim to pull on the breast tissue. The expansion force becomes a function of the elastic recoil properties of the rim/flexible dome construct.

The present invention also provides methods of use of the expanders. For example, one method provides reducing shear stress including positioning a device having a shell and a rim extending from the shell configured for contact with a body of a patient, wherein the rim is non-adherently positioned on the body so that upon application of a distracting force within the shell, the rim spreads laterally outwardly with respect to the shell such that shear stress is reduced at a junction between skin inside the shell and the skin held down by the rim. The method can include providing a distractive force by elastic recoil of one or both of the shell or rim or by applying a vacuum within the shell.

Persons skilled in the art will understand that the elements and features shown or described in connection with one embodiment may be combined with those of another embodiment without departing from the scope of the present disclosure and will appreciate further features and advantages of the presently disclosed subject matter based on the description provided.

While the present invention has been described with reference to the specific embodiments thereof, which constitute non-limiting examples, it should be understood by those skilled in the art that various changes and modifications may be made and equivalents may be substituted without departing from the spirit and scope of the invention as defined in the appended claims. In addition, many modifications may be made to adopt a particular situation, material, composition of matter, process, process step or steps, to the objective spirit and scope of the present invention. All such modifications are intended to be within the scope of the claims appended hereto.

Where a range of values is provided, it is understood that each intervening value within the stated range is encompassed within the invention.

Throughout the present disclosure, terms such as "approximately," "about," "generally," "substantially," and the like should be understood to allow for variations in any numerical range or concept with which they are associated. For example, it is intended that the use of terms such as "approximately," "about" and "generally" should be understood to encompass variations on the order of 25%, or to allow for manufacturing tolerances and/or deviations in design.

Although terms such as "first," "second," "third," etc., may be used herein to describe various operations, elements, components, regions, and/or sections, these operations, elements, components, regions, and/or sections should not be limited by the use of these terms in that these terms are used to distinguish one operation, element, component, region, or section from another. Thus, unless expressly stated otherwise, a first operation, element, component, region, or section could be termed a second operation, element, component, region, or section without departing from the scope of the present.

Each and every claim is incorporated as further disclosure into the specification and represents embodiments of the present disclosure. Also, the phrases "at least one of A, B, and C" and "A and/or B and/or C" should each be interpreted to include only A, only B, only C, or any combination of A, B, and C.

What is claimed is:

1. A brassiere comprising:
 a) a first aperture b) a second aperture;
 c) a first shell having a first flexible rim extending downwardly and laterally outwardly therefrom, the first aperture dimensioned and configured to receive one or both of the first shell and first rim, the first rim non-fixedly and non-adhesively positionable in contact with skin of a wearer and having curved inner and outer surfaces; and
 d) a second shell having a second flexible rim extending downwardly laterally outwardly therefrom, the second aperture dimensioned and configured to receive one or both of the second shell and second rim, the second rim non-fixedly and non-adhesively positionable in contact with the skin of the wearer;
 e) wherein the first and second rims are of less hardness than the first and second shells and are slidable outwardly while maintaining contact with the skin, the first and second rims slidable outwardly from a first position wherein the first and second rims extend outwardly from the first and second shells respectively and a second position wherein the first and second rims extend further outwardly from the first and second shells respectively; and
 f) wherein the first and second rims have an initial concave lower surface configured to contact the skin of the wearer, the concave lower surface deformable upon application of vacuum to a second convex surface remaining in contact with the skin.

2. The brassiere of claim 1, further comprising brassiere straps, wherein when distractive force is applied to the skin of the wearer within the first and second shells, the brassiere straps allow the first and second rims to slide laterally outwardly while forcing the first and second rims to maintain skin contact.

3. The brassiere of claim 2, wherein the distractive forces are applied by an external vacuum in communication with the first and second shells.

4. The brassiere of claim 2, wherein the distractive forces are applied by elastic recoil of the first and second shells.

5. The brassiere of claim 1, further comprising reinforcement members to maintain feathered peripheral edges of the first and second rims in firm contact with the skin around a breast of the patient to ensure a vacuum seal, a thinnest portion of the peripheral edge being at a distalmost edge and the reinforcement members extending to a distal edge of the first and second rims.

6. The brassiere of claim 1, wherein the first and second rims are composed of low durometer synthetic rubber.

7. The brassiere of claim 1, wherein the first and second rims have a feathered down periphery to increase contact area with the skin and an inner surface of the feathered down periphery is smooth and uninterrupted.

8. The brassiere of claim 1, wherein the first shell is removable from the first rim and the second shell is removable from the second rim, the first and second shells interchangeable with shells of a different depth, the first shell being harder than the first rim and the second shell being harder than the second rim.

9. A brassiere comprising:
 a) a first aperture
 b) a second aperture;
 c) a first shell having a first rim extending laterally outwardly therefrom, the first aperture dimensioned and configured to receive one or both of the first shell and first rim, the first rim non-fixedly and non-adhesively positionable in contact with skin of a wearer and being asymmetric with a medial side having a length less than a length of a lateral side, the lateral side configured to wrap around the skin of the wearer, the lateral side having a deeper concavity than the medial side; and d) a second shell having a second rim extending laterally outwardly therefrom, the second aperture dimensioned and configured to receive one or both of the second shell and second rim, the second rim non-fixedly and non-adhesively positionable in contact with the skin of the wearer;

e) wherein each of the first and second rims increasingly spread laterally under increasing pressure.

10. The brassiere of claim 9, wherein the first and second rims are composed of a low durometer synthetic rubber material.

11. The brassiere of claim 9, wherein the first and second rims in a pre-vacuum condition have an inward camber angling downward and inward from a horizontal plane to enhance gripping of the body of the wearer.

12. The brassiere of claim 9, wherein distractive forces are applied by an external vacuum in communication with the shell.

13. The brassiere of claim 9, wherein each of the first and second rims has a feathered down periphery to increase contact area with the skin, a thinnest portion of the periphery being at the distalmost edge.

14. A brassiere comprising:
a) a first aperture
b) a second aperture;
c) a first shell having a first rim extending laterally outwardly therefrom, the first aperture dimensioned and configured to receive one or both of the first shell and first rim, the first rim non-fixedly positionable in contact with skin of a wearer; and d) a second shell having a second rim extending laterally outwardly therefrom, the second aperture dimensioned and configured to receive one or both of the second shell and second rim, the second rim non-fixedly positionable in contact with the skin of the wearer;

e) wherein each of the first and second rims has a pre-vacuum concave condition having a downwardly extending concave lower surface configured to contact the skin of the wearer and at least a segment of the concave lower surface deforms upon application of vacuum to a convex condition to invert to a downwardly extending convex surface configured to contact the skin of the wearer.

15. The brassiere of claim 14, wherein the first and second rims change angle from a more vertical to a more horizontal with application of pressure.

16. The brassiere of claim 14, wherein the first and second rims have a feathered down periphery to increase contact area with the skin, the feathered down periphery increasingly narrowing to a distalmost end.

17. The brassiere of claim 16, further comprising reinforcing members to maintain feathered peripheral edges of the first and second rims in firm contact with the skin.

18. The brassiere of claim 14, wherein the first and second shells are dome-shaped.

19. The brassiere of claim 14, wherein the first and second rims have a tapering edge in the concave and convex conditions.

* * * * *